US008431356B2

(12) United States Patent
Thomas et al.

(10) Patent No.: US 8,431,356 B2
(45) Date of Patent: Apr. 30, 2013

(54) FLUORESCENCE RESONANCE ENERGY TRANSFER ASSAYS FOR SARCO/ENDOPLASMIC RETICULUM CALCIUM ATPASE AND PHOSPHOLAMBAN

(75) Inventors: David D. Thomas, Minneapolis, MN (US); Razvan L. Cornea, Woodbury, MN (US); Krisztina M. Zsebo, Santa Barbara, CA (US)

(73) Assignees: Regents of the University of Minnesota, Saint Paul, MN (US); Celladon Corporation, La Jolla, CA (US)

( * ) Notice: Subject to any disclaimer, the term of this patent is extended or adjusted under 35 U.S.C. 154(b) by 0 days.

(21) Appl. No.: 13/145,787

(22) PCT Filed: Jan. 21, 2010

(86) PCT No.: PCT/US2010/021564

§ 371 (c)(1), (2), (4) Date: Oct. 10, 2011

(87) PCT Pub. No.: WO2010/085514

PCT Pub. Date: Jul. 29, 2010

(65) Prior Publication Data

US 2012/0021926 A1 Jan. 26, 2012

Related U.S. Application Data

(60) Provisional application No. 61/146,608, filed on Jan. 22, 2009, provisional application No. 61/229,245, filed on Jul. 28, 2009.

(51) Int. Cl.
*C12Q 1/21* (2006.01)

(52) U.S. Cl.
USPC .......... 435/21

(58) Field of Classification Search .......... 435/21
See application file for complete search history.

(56) References Cited

U.S. PATENT DOCUMENTS

| | | | | |
|---|---|---|---|---|
| 6,265,421 | B1 * | 7/2001 | Pystynen et al. | 514/317 |
| 6,540,996 | B1 * | 4/2003 | Zwaal et al. | 424/93.21 |
| 2011/0245167 | A1 * | 10/2011 | Xie et al. | 514/7.5 |

FOREIGN PATENT DOCUMENTS

| | | | |
|---|---|---|---|
| WO | WO 2005/003783 | A1 | 1/2005 |
| WO | WO 2006/063128 | A2 | 6/2006 |

OTHER PUBLICATIONS

Winters D. et al. Interdomain Fluorescence Resonance Energy Transfer in SERCA . . . Biochemistry 47(14)4246-4256, 2008.*

Robia S. et al. Forster Transfer Recovery Reveals That Phospholamban Exchanges Slowly . . . Circulation Research 101(11)1123-1129, 2007.*

Mueller B. et al. Direct Detection of Phospholamban and SERCA Interaction . . . Biochemistry 43:8754-8765, 2004.*

Kelly E. et al. Phospholamban Oligomerization, Quaternary Structure . . . J of Biological Chemistry 283(18)12202-11, 2008.*

Winters D. SERCA Domain Dynamics as Detected by FRET. Dissertation Abstracts Int B 69(6)3572, 2008.*

Mueller B. Direct Detection of Phospholamban and SERCA Interaction in Membranes Using FRET. Dissertation Abstracts Int. B 65(8)4010, 2005.*

Bidwell et al., "FRET From SERCA to Phospholamban Is Decreased by Thapsigargin and Anti-PLB Antibody, But Not by Calcium," Biophysical Journal, vol. 96, No. 3, 738-POS, p. 143A (Feb. 10, 2009).

Mueller et al., "Direct Detection of Phospholamban and Sarcoplasmic Reticulum Ca-ATPase Interaction in Membranes Using Fluorescence Resonance Energy Transfers," Biochemistry, vol. 43, No. 27, pp. 8754-8765 (Jul. 13, 2004).

Chen et al., "Concerted but Noncooperative Activation of Nucleotide and Actuator Domains of the Ca-ATPase upon Calcium Binding", Biochemistry, (2008), vol. 47, pp. 12448-12456.

Cornea et al., "High-Throughput FRET Assay Yields Allosteric SERCA Activators", Journal of Biomolecular Screening, (2012), pp. 1-10.

Hou et al., "2-Color Calcium Pump Reveals Closure of the Cytoplasmic Headpiece with Calcium Binding", PLoS One, (2012), vol. 7, Issue 7, e40369, Total pp. 10.

Johnson, Jr., Robert G., "Pharmacology of the Cardiac Sarcoplasmic Reticulum Calcium ATPase-Phospholamban Interaction", Annals New York Academy of Sciences, (1998), vol. 853, pp. 380-392.

Satoh et al., "Highly Cooperative Dependence of Sacro/Endoplasmic Reticulum Calcium ATPase (SERCA) 2a Pump Activity on Cytosolic Calcium in Living Cells", The Journal of Biological Chemistry, (2011), vol. 286, No. 23, pp. 20591-20599.

Thomas et al., "Direct Spectroscopic Detection of Molecular Dynamics and Interactions of the Calcium Pump and Phospholamban", Annals New York Academy of Sciences, (1998), vol. 853, p. 186-194.

Winters et al., "Interdomain Fluorescence Resonance Energy Transfer of SERCA Probed by Cyan-Fluorescent Protein Fused to the Actuator Domain", Biochemistry, (2008), vol. 47, pp. 4246-4256.

Index of the vol. 853 of the Annals of the New York Academy of Sciences, (1998), Total pp. 39.

* cited by examiner

*Primary Examiner* — Ralph Gitomer
(74) *Attorney, Agent, or Firm* — Jones Day

(57) ABSTRACT

Provided herein are methods for identifying molecules capable of modulating SERCA, the SERCA-PLB complex or the microenvironment of the complex. An exemplary assay provided herein is fluorescence resonance energy transfer (FRET). Also provided herein are FRET assays that are optimized for high-throughput screening (HTS) for identifying small molecules that modulate SERCA or the SERCA-PLB complex. Further provided are kits for carrying out said methods for identifying molecules.

20 Claims, 4 Drawing Sheets

Figure 1. Effect of CDN1001, 1054, 1234 on IAEDANS-SERCA Time-Resolved Fluorescence
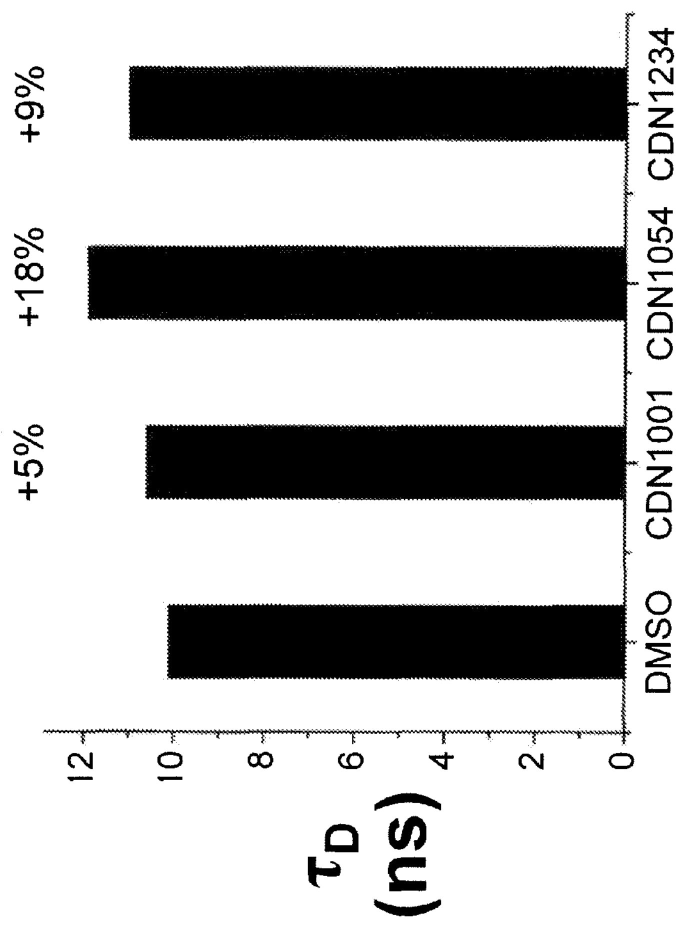
$\tau_D$ (ns)

Figure 2. CDN Effects on Time-Resolved FRET from IAEDANS-SERCA to TNP-ADP
A. Fluorescence Lifetimes
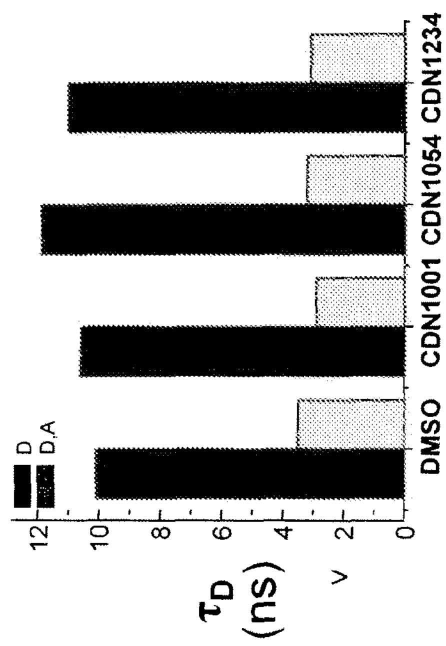
B. FRET = 1- τDA/ τD
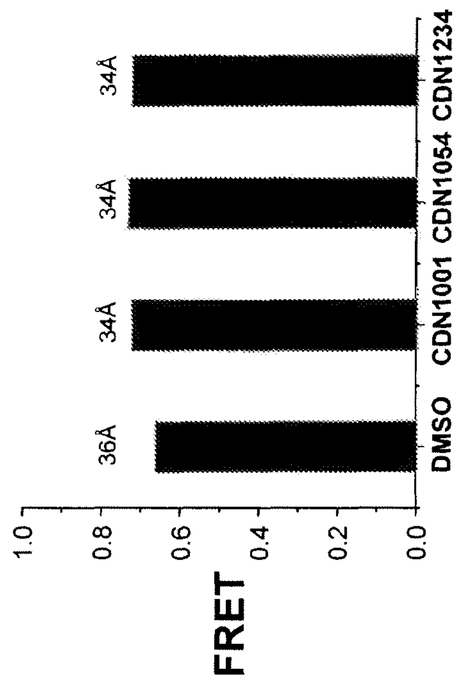

Figure 3. CDN1054 Dose Response of the Fluorescence Lifetimes of IAEDANS-SERCA
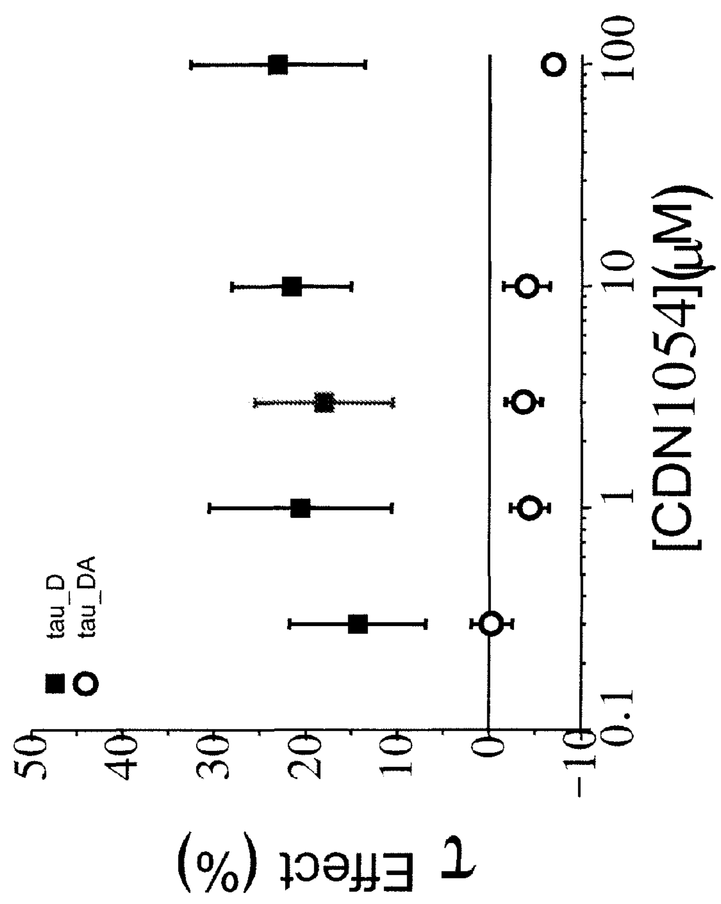

Figure 4. CDN1054 Dose Response Effects of Time-Resolved FRET from IAEDANS-SERCA to TNP-ADP
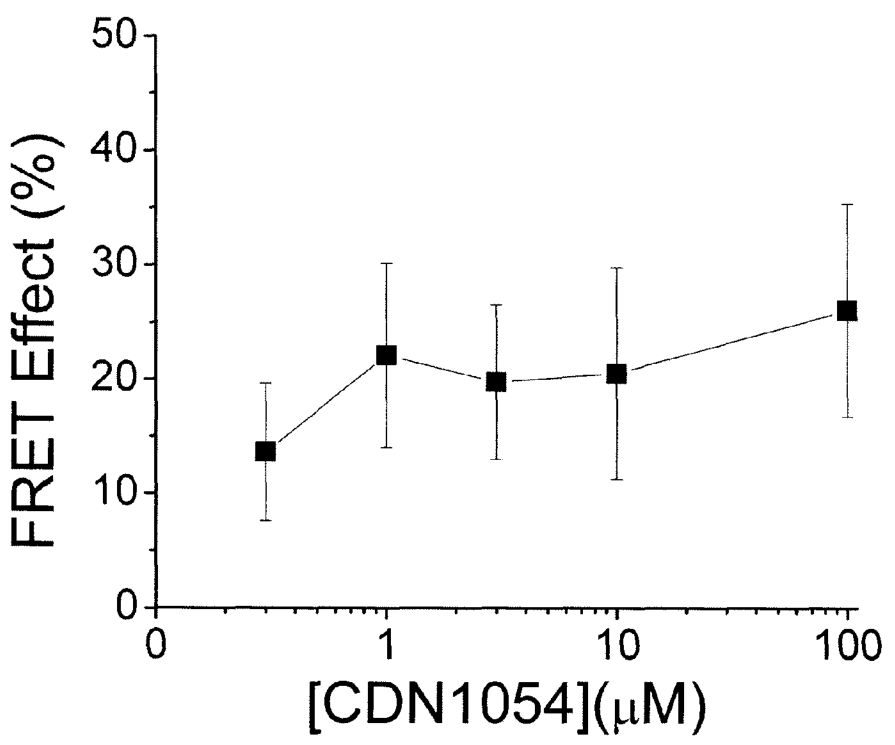

FLUORESCENCE RESONANCE ENERGY TRANSFER ASSAYS FOR SARCO/ENDOPLASMIC RETICULUM CALCIUM ATPASE AND PHOSPHOLAMBAN

RELATED APPLICATIONS

CROSS-REFERENCE TO RELATED APPLICATIONS

This application is a United States national stage application and claims the benefit of PCT application Serial No. PCT/US2010/021564, filed Jan. 21, 2010, which claims priority to U.S. Provisional Patent Application Nos. 61/146,608, filed Jan. 22, 2009, and 61/229,245, filed Jul. 28, 2009, both entitled "FLUORESCENCE RESONANCE ENERGY TRANSFER ASSAYS FOR SARCO/ENDOPLASMIC RETICULUM CALCIUM ATPASE AND PHOSPHOLAMBAN." The disclosures of the above-referenced applications are incorporated by reference herein in their entirety.

FEDERALLY SPONSORED RESEARCH

This invention was made with U.S. government support under Grant No. R01 GM27906 awarded by The National Institutes of Health. The U.S. government has certain rights in the invention.

FIELD

Provided herein are methods for identifying molecules that modulate sarco/endoplasmic reticulum calcium ATPase (SERCA), the SERCA-phospholamban (PLB) complex or the microenvironment of the complex. An exemplary assay provided herein is fluorescence resonance energy transfer (FRET). Also provided herein are FRET assays that are optimized for high-throughput screening (HTS) for identifying molecules that modulate SERCA, the SERCA-PLB complex or the microenvironment of the complex, in the presence or absence of a membrane. Further provided are kits for carrying out said methods for identifying molecules.

BACKGROUND

Muscle contraction is regulated by interactions of free cytosolic calcium with calcium-activated proteins such as troponin C or calmodulin. These proteins initiate a cascade of events leading to cell shortening and muscle contraction. SERCA is a membrane protein that terminates or prevents the muscle contraction. This protein transfers cytosolic calcium against the concentration gradient into the sarcoplasmic reticulum (SR) and is present in many tissue and development-specific isoforms. Cancer is a disease that in many cases confers resistance to apoptosis. SERCA can also transfer cytosolic calcium against the concentration gradient into the endoplasmic reticulum, thereby modulating the intracellular calcium concentration and reversing resistance to apoptosis in cancer cells.

PLB is a small membrane protein that inhibits SERCA at submicromolar calcium concentration. The inhibition of SERCA by PLB can be relieved either by phosphorylation of PLB or by elevation of calcium concentration to the micromolar range. Through its inhibitory effects on SERCA, PLB represses both the rates of relaxation and contraction of the muscle cells. Because SERCA and PLB play a major role in muscle contraction, abnormal SERCA or PLB activity as well as SERCA-PLB interactions have been implicated in a wide variety of muscle diseases. For example, enhanced inhibition of SERCA by PLB has been associated with heart failure. (Delling et al., (2000) *Nature Medicine* 6:942-943; Kiriazis et al., (2000) *Annu. Rev. Physiol.* 62:321-351). The R9C mutation of PLB in humans was directly linked to development of dilated cardiomyopathy and progression to heart failure in young adults (Schmitt et al., (2003) *Science* 299, 1410-1413).

Certain molecules that modulate the SERCA-PLB complex or its microenvironment bind SERCA directly, even in the absence of PLB. In several different cell types, excessive cytosolic calcium has been shown to induce apoptosis. Id.; see also Nicotera et al., *Cell Calcium* (1998) 23: 173-180. For example, Christensen et al. reported that the growth of LNCaP prostate cancer cells in mice was inhibited by administration of thapsigargin, which is a SERCA inhibitor. *Bioorg. Med. Chem.* 14 (2006) 2810-2815, incorporated herein by reference in its entirety. The authors attributed this observed inhibition to the potency of thapsigargin as an inhibitor of SERCA. Id. at 2810. Specifically, the authors explained that SERCA inhibition induces an increase in cytosolic calcium concentration, which eventually causes apoptosis. Id. In another example, cyclooxygenase 2 (COX-2) inhibitors, such as celecoxib, have emerged as potential anticancer agents. Schönthal, *Cancer Lett.* (2008), doi: 10.1016/j.canlet.2008.07.005, the entirety of which is incorporated herein by reference. It is thought that the inhibition of COX-2 is not involved in the anticancer effect of celecoxib; rather, celcoxib inhibits tumor growth via inhibition of SERCA. Id. at 4-5. Schönthal is now taking advantage of this discovery by designing and synthesizing new compounds that even more effectively target SERCA, which may lead to the discovery of anticancer agents. Id. Based on theses findings, it is contemplated that molecules capable of regulating SERCA, the SERCA-PLB complex or its microenvironment would have broad applications for treating SERCA- or PLB-related diseases.

Therefore, a consistent and reliable method of identifying molecules that modulate SERCA, the SERCA-PLB complex or the microenvironment of the complex would merit further investigation. Due to the complexity of membrane proteins such as SERCA and PLB, it has been very difficult to produce a synthetic system that can recapitulate the cellular interactions in a large-scale reproducible manner. Moreover, observation of modulated SERCA-PLB complex or its microenvironment has been limited, for example, by unsuitable FRET potency or strong SERCA and PLB interactions that cannot be easily disrupted. Thus, a HTS assay that is capable of performing said method in a membrane would be valuable in clinical and pharmaceutical research for SERCA or PLB-related diseases.

SUMMARY

Provided herein are methods for identifying molecules that modulate SERCA, the SERCA-PLB complex or the microenvironment of the complex. An exemplary assay provided herein is FRET. Also provided herein are FRET assays that are optimized for HTS for identifying molecules that modulate SERCA, the SERCA-PLB complex or the microenvironment of the complex, in the presence or absence of a membrane. Further provided are kits for carrying out said methods for identifying molecules.

Thus, provided herein are methods for identifying a compound that modulates SERCA, comprising: (a) providing SERCA labeled with a first chromophore at a first position; (b) exciting the chromophore; and (c) measuring the fluorescence lifetime of the first chromophore; wherein a difference between the fluorescence lifetime in the presence of the test compound and the fluorescence lifetime in the absence of the test compound indicates that the test compound modulates SERCA, such that the fluorescence lifetime of the chromophore is altered.

Also provided are methods for identifying a compound that modulates SERCA, comprising: (a) providing SERCA labeled with a first chromophore at a first position and a second chromophore at a second position, wherein the second position is different from the first position, and wherein the first and the second chromophores can be used for energy transfer; (b) exciting either the first or the second chromophore; and (c) measuring FRET between the chromophores; wherein a difference between FRET in the presence of the test compound and FRET in the absence of the test compound indicates that the test compound modulates SERCA, such that the energy transfer between the two chromophores is altered.

Further provided are methods for identifying a compound that modulates the SERCA-PLB complex or its microenvironment, comprising: (a) providing SERCA labeled with a first chromophore; (b) providing PLB labeled with a second chromophore, wherein the PLB is WT-PLB or a PLB derivative that gives a FRET potency suitable for HTS, and wherein the chromophores can be used for energy transfer; (c) contacting the SERCA of step (a) with the PLB of step (b) in the presence of a test compound and one or more lipids; (d) exciting either the first or the second chromophore; and (e) measuring FRET between the chromophores; wherein a difference between FRET in the presence of the test compound and FRET in the absence of the test compound indicates that the test compound modulates the SERCA-PLB complex or its microenvironment, such that the energy transfer between the two chromophores is altered.

Further provided are kits for carrying out methods disclosed herein, in a container, and instructions for use.

Further provided herein are kits for identifying a compound that modulates the SERCA-PLB complex or its microenvironment, comprising: (a) SERCA labeled with a first chromophore; and (b) PLB labeled with a second chromophore; wherein the PLB is WT-PLB or a PLB derivative that gives a FRET potency suitable for HTS, and wherein the chromophores can be used for energy transfer.

Additionally provided are kits for identifying a compound that modulates the SERCA-PLB complex or its microenvironment, comprising: (a) a first oligonucleotide expressing SERCA; (b) a second oligonucleotide expressing PLB, and (c) a first and a second chromophore provided for labeling, wherein the PLB is WT-PLB or a PLB derivative that gives a FRET potency suitable for HTS, and wherein the chromophores can be used for energy transfer.

DEFINITIONS

To facilitate understanding of the disclosure set forth herein, a number of terms are defined below.

Generally, the nomenclature used herein and the laboratory procedures described herein are those well known and commonly employed in the art. Unless defined otherwise, all technical and scientific terms used herein generally have the same meaning as commonly understood by one of ordinary skill in the art to which this disclosure belongs. All patents, applications, published applications and other publications are incorporated by reference in their entirety. In the event that there is a plurality of definitions for a term used herein, those in this section prevail unless stated otherwise.

The term "FRET" refers to energy transfer processes that occur between two chromophores. The chromophores as used herein comprise, for example, fluorescent, luminescent and other non-fluorescent components. "FRET," "fluorescence resonance energy transfer," "Förster resonance energy transfer" and "resonance energy transfer" are used interchangeably herein.

The term "time-resolved FRET" as used herein refers to energy transfer processes that occur between two chromophores based on time-resolved detection of the spectra.

The term "steady-state FRET" as used herein refers to energy transfer processes that occur between two chromophores based on steady state detection of the spectra. The term "steady-state" as used herein refers to a situation in which all state variables are constant.

The term "intramolecular FRET" as used herein refers to energy transfer processes that occur between two chromophores that are limited within the structure of a single molecule (e.g., FRET within SERCA).

The term "intermolecular FRET" as used herein refers to energy transfer processes that occur between two or more molecules (e.g., FRET between SERCA and PLB).

The term "fluorescence lifetime" refers to the average time the molecule stays in its excited state before emitting a photon.

The term "labeled" refers to a compound or composition that is specifically associated, by covalent bonding or noncovalent interactions, with a target. A label may be detectable directly, for example, the label can be a fluorescent or phosphorescent molecule (e.g., FITC, rhodamine, lanthanide phosphors) or the label can be a radioisotope (e.g., $^{3}H$, $^{14}C$, $^{32}P$, $^{35}S$, $^{125}I$, $^{131}I$), or indirectly, for example, by enzymatic activity (e.g., horseradish peroxidase, beta-galactosidase, luciferase, alkaline phosphatase). Incorporation of a label can be achieved by a variety of means known in the art, for example, by use of high binding affinity between two molecules such as an enzyme and its substrate (e.g., ATPase and ATP), streptavidin and biotin or an antigen or epitope and an antibody. Other means include, by way of illustration, the use of radiolabeled or biotinylated nucleotides in polymerase-mediated primer extension reactions or epitope-tagging via recombinant expression or synthetic means. Labels can be attached directly or via spacer arms or linkers of various lengths. Any of a wide variety of labeled reagents can be used for purposes of the methods and kits provided herein. The term "label" can also refer to as a "tag," which can bind specifically to a labeled molecule.

The term "FRET potency" refers to the change in FRET efficiency E resulting from a perturbation. Such perturbation can be triggered, for example, by addition of a modulating compound to SERCA in the presence or absence of PLB. For the HTS methods and kits provided herein, the suitable FRET potency is one which can be detected by modulating SERCA, the SERCA-PLB complex or the microenvironment of the complex. In certain embodiments of the methods and kits provided herein, a suitable FRET potency is one that is within the dynamic range of the measuring instrument (e.g., fluorescence plate reader).

The term "can be disrupted" as used herein refers to the likelihood of dissociation of the SERCA-PLB complex. In certain embodiments, the likelihood of dissociation of the SERCA-PLB complex can be illustrated by the functional and/or FRET change in a competitive setting. For example, the likelihood of dissociation of the SERCA-PLB complex can be measured by the functional relief of SERCA and/or the FRET relief in the presence of loss-of-function (LOF) PLB derivatives competing with WT-PLB or a tested PLB derivative. The greater the functional and/or FRET relief is, the more likely that the SERCA-PLB interaction can be disrupted. For the HTS methods and kits provided herein, the suitable binding affinity of SERCA to a PLB derivative is one with which the change in FRET due to the association and dissociation of SERCA and PLB can be detected by a measuring instrument. In certain embodiments, the binding affinity of SERCA to PLB is one that is within the dynamic range of the measuring instrument. In certain embodiments, the SERCA-PLB interaction can be disrupted when the interaction is such that a range of test compounds give a range of results. In certain embodiments, the SERCA-PLB interaction can be disrupted, if the binding affinity of SERCA to PLB is within one order of magnitude of that of SERCA to WT-PLB.

The term "SERCA-PLB complex" refers to the structure formed when SERCA interacts or associates with PLB.

The terms "modulate," "modulation" and "modulating" refer to the capacity to alter a measurable functional property of biological activity or process (e.g., interactions between different SERCA functional domains; interactions between SERCA and PLB).

In certain embodiments, modulating the SERCA-PLB complex or its microenvironment refers to an alteration of SERCA-PLB interaction by a compound, for example, perturbation or disruption of the interaction between SERCA and PLB. Examples of modulating the SERCA-PLB complex or its microenvironment include, by way of illustration, through modulating the lipids (e.g., microenvironment of the lipids). In certain embodiments, modulating the SERCA-PLB complex or its microenvironment refers to an alteration of SERCA-PLB interaction by a compound, for example, perturbation or disruption of the interaction between SERCA and PLB. In certain embodiments, modulating the SERCA-PLB complex or its microenvironment is achieved by introducing a perturbation to SERCA-PLB interaction (e.g., addition of a modulating compound). In certain embodiments, modulating the SERCA-PLB complex or its microenvironment refers to modulating SERCA (e.g., altering the conformation or a measurable functional or biological property of SERCA).

Modulation of SERCA includes, but are not limited to, modulating the secondary structure and/or the tertiary structure of SERCA, and activating or inhibiting SERCA activity. In certain embodiments, modulating SERCA means an alteration of the interactions between different SERCA functional domains by a compound (e.g., change of the distance between different SERCA domains). In certain embodiments, modulating SERCA is achieved by changing the distance between different SERCA domains (e.g., addition of a modulating compound). In certain embodiments, a compound modulating SERCA also modulates the SERCA-PLB complex or its microenvironment.

In certain embodiments, a compound modulates SERCA, the SERCA-PLB complex or the microenvironment of the complex through modulating PLB. Non-limiting examples of modulating PLB include modulating the secondary structure and/or the tertiary structure of PLB, activating or inhibiting PLB activity. In certain embodiments, a compound modulates PLB through direct binding to PLB.

The term "microenvironment" as used herein refers to the physical properties of molecules or components surrounding the SERCA-PLB complex (e.g., within several nanometers of the SERCA-PLB complex). Such molecules or components include, by way of example only, water, buffer, solvent and lipids.

As used herein, the term "chromophore" refers to a substituent which, with another chromophore, can be used for energy transfer (e.g., FRET assay).

The term "fluorescent component" as used herein refers to a component capable of absorbing energy and then re-emitting at least some fraction of that energy as light over time. In certain embodiments, a fluorescent component is a discrete compound, molecule, naturally fluorescent protein and macromolecular complexes or mixture of fluorescent and non-fluorescent compounds or molecules. In certain embodiments, a fluorescent component refers to components that exhibit long-lived fluorescence decay such as lanthanide ions and lanthanide complexes with organic ligand sensitizers, which absorb energy and then re-emit the energy over milliseconds.

The term "luminescent component" as used herein refers to a component capable of absorbing energy, such as electrical (e.g., electro-luminescence), chemical (e.g., chemi-luminescence) or acoustic energy and then emitting at least some fraction of that energy as light over time.

The term "component" as used herein includes discrete compounds, molecules, bioluminescent proteins and macromolecular complexes or mixtures of luminescent and non-luminescent compounds or molecules that act to cause the emission of light.

The term "naturally fluorescent protein" refers to a protein capable of forming a highly fluorescent, intrinsic chromophore either through the cyclization and oxidation of internal amino acids within the protein or via the enzymatic addition of a fluorescent co-factor. The term "naturally fluorescent protein" includes wild-type fluorescent proteins and mutants that exhibit altered spectral or physical properties. The term does not include proteins that exhibit weak fluorescence by virtue only of the fluorescence contribution of non-modified tyrosine, tryptophan, histidine and phenylalanine groups within the protein.

The term "naturally occurring" or "native" when used in connection with biological materials such as nucleic acid molecules, polypeptides, protein and host cells, refers to those which are found in nature and not manipulated by a human being.

The term "wild-type" or "WT" refers to the most typical form of an organism, strain, gene, polypeptide, protein or characteristic as it occurs in nature.

The term "loss-of-function mutation" refers to a mutation which causes reduced or abolished function of an organism, strain, gene, polypeptide, protein or characteristic as it occurs in nature.

The term "gain-of-function mutation" refers to a mutation that causes enhanced or activated function of an organism, strain, gene, polypeptide, protein or characteristic as it occurs in nature.

The term "organism" as used herein refers to any forms of life beings.

The terms "modified" polypeptide or protein, polypeptide or protein "variant," polypeptide or protein "derivative," "mutated" polypeptide or protein, "mutant" polypeptide or protein, polypeptide or protein "mutant," and "recombinant" polypeptide or protein are used interchangeably and refer to any variations of a polypeptide having an amino acid sequence that differs from the wild-type polypeptide or protein. Examples of modifications of a polypeptide or protein include, but are not limited to, additions, deletions and substitutions of one or more of amino acid residues. The modifications can be made by any method known in the art and many such methods are well known and routine for the skilled artisan. For example, but not by way of limitation, amino acid substitutions, deletions and insertions can be accomplished using any well-known PCR-based technique. Amino acid substitutions can be made by site-directed mutagenesis (see, for example, Zoller and Smith, (1982) *Nucl. Acids Res.* 10:6487-6500; Kunkel, (1985) *Proc. Natl. Acad. Sci USA* 82:488, which are hereby incorporated by reference in their entireties). As such, modified SERCA refers to a SERCA polypeptide or protein that has a different amino acid sequence from the WT-SERCA, and is used interchangeably with "SERCA variant," "SERCA derivative," "mutated SERCA," "SERCA mutant" or "mutant SERCA." Similarly, modified PLB refers to PLB polypeptide or protein that has a different amino acid sequence from the WT-PLB, and is used interchangeably with "PLB variant," "PLB derivative," "mutated PLB" or "mutant PLB."

In the context of a peptide, polypeptide or protein, the term "fragment" as used herein refers to a peptide or polypeptide that comprises less than the full length amino acid sequence. Such a fragment may arise, for example, from a truncation at the amino terminus, a truncation at the carboxyl terminus, and/or an internal deletion of a residue(s) from the amino acid sequence. Fragments may, for example, result from alternative RNA splicing or from in vivo protease activity. In certain embodiments, SERCA fragments include polypeptides comprising an amino acid sequence of any number of amino acid residues. In certain embodiments, SERCA fragments include polypeptides comprising an amino acid sequence of at least 15 contiguous amino acid residues, at least 25 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250 contiguous amino acid residues, at least 500 contiguous amino acid residues, at least 750 contiguous amino acid residues, at least 900 contiguous amino acid residues, at least 950 contiguous amino acid residues, and at least 975 contiguous amino acid residues of the amino acid sequence of SERCA. In certain embodiments, PLB fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, and at least 50 contiguous amino acid residues of the amino acid sequence of PLB.

An "isolated" or "purified" polypeptide or protein is substantially free of cellular material or other contaminating proteins from the cell or tissue source from which the protein is derived, regardless of whether the protein is naturally occurring or engineered into the cell (e.g., recombinantly produced). In certain embodiments, an "isolated" or "purified" polypeptide or protein refers to a polypeptide or protein that is substantially free of chemical precursors or other chemicals when chemically synthesized.

The term "SR" refers to sarcoplasmic reticulum, which is a special type of smooth endoplasmic reticulum found in the muscle cells. The SR stores calcium ions and releases the ions when the muscle cell is stimulated.

The term "ATPase" refers to a protein that catalyzes ATP hydrolysis, i.e., the conversion of adenosine triphosphate (ATP) into adenosine diphosphate (ADP) and a free phosphate ion.

The term "calcium ATPase" is a form of ATPase that transfers calcium at the expense of ATP hydrolysis. The terms "calcium ATPase," "$Ca^{2+}$ ATPase," "calcium-transporting ATPase" and "$Ca^{2+}$-transporting ATPase" are used interchangeably herein.

The term "SERCA" refers to the polypeptide or protein of SR Ca-ATPase. WT-SERCA as used herein comprises the wild-type amino acid sequence of SERCA (Autry et al., (1997) *J. Biol. Chem.* 272:15872-15880). Modified SERCA refers to a SERCA polypeptide or protein that has a different amino acid sequence from the WT-SERCA, and is used interchangeably with "SERCA variant," "SERCA derivative," "mutated SERCA," "SERCA mutant" or "mutant SERCA." Unless otherwise specified, the term "SERCA" refers to any isoform of wild-type or modified SERCA from any source.

The term "high-throughput screening" or "HTS" refers to a method drawing on different technologies and disciplines, for example, optics, chemistry, biology or image analysis to permit rapid, highly parallel biological research and drug discovery.

The term "PLB" refers to the polypeptide or protein of phospholamban. Unless otherwise specified, WT-PLB as used herein comprises the wild-type amino acid sequence of Swiss-Prot P61012.1 (corresponding to the nucleotide sequence of Genbank NP__001003332), or Swiss-Prot P26678.1 (corresponding to the nucleotide sequence of Genbank NP__002658). Modified PLB refers to PLB polypeptide or protein that has a different amino acid sequence from the WT-PLB, and is used interchangeably with "PLB variant," "PLB derivative," "mutated PLB" or "mutant PLB." Unless otherwise specified, the term "PLB" refers to any isoforms of wild-type or modified PLB from any source.

As used herein, the term "fast-twitch skeletal muscle fiber" or "fast-twitch fiber" refers to a type of muscle fiber that is capable of performing more powerful and shorter contractions. This type of muscle fiber metabolizes energy more quickly and has a lower capillary to volume ratio. "Fast-twitch skeletal fiber" can also be referred to as "white" or "type II" fiber. The term "slow-twitch skeletal muscle fiber" or "slow-twitch fiber" refers to a type of muscle fiber that sustains slow but long-lived muscular contractions from aerobic energy. This type of muscle fiber metabolizes energy more slowly and has a greater capillary to volume ratio. "Slow-twitch skeletal fiber" can also be referred to as "red" or "type I" fiber. The fast-twitch and slow-twitch fibers are distributed throughout the muscles of the body. The percentage distribution is determined genetically.

As used herein, the term "body part" refers to any part of the body. The term is meant to include without limitation any body part, whether that body part is described in anatomic, physiologic or topographic terms. A body part can be of any size, whether macroscopic or microscopic. The term "body part" can refer to a part of the body in vivo or ex vivo. The term ex vivo is understood to refer to any body part removed from body, whether that body part is living or is non-living. An ex vivo body part comprises an organ for transplantation or for replantation. An ex vivo body part comprises a pathological or a forensic specimen. An ex vivo body part may also refer to a body part in vitro. The term "body part" may refer to the anatomic components of an organ. For example, the appendix is understood to be an anatomic component of the organ known as the intestine.

"Lipid" refers to a synthetic or naturally-occurring amphipathic compound which comprises a hydrophilic component and a hydrophobic component. Lipids as used herein include without limitations, fatty acids, glycerolipids, glycerophospholipids, sphingolipids, glycolipids, polyketides, sterol lipids, prenol lipids and a derivative thereof. “Lipid composition” refers to a composition which comprises at least a lipid compound. Exemplary lipid compositions include suspensions, emulsions, micelles, and vesicular compositions. The lipids as used herein may be in the form of a monolayer or bilayer, and the mono- or bilayer lipids may be used to form one or more mono- or bilayers.

The term “about” or “approximately” means an acceptable error for a particular value as determined by one of ordinary skill in the art, which depends in part on how the value is measured or determined. In certain embodiments, the term “about” or “approximately” means within 1, 2, 3, or 4 standard deviations. In certain embodiments, the term “about” or “approximately” means within 50%, 20%, 15%, 10%, 9%, 8%, 7%, 6%, 5%, 4%, 3%, 2%, 1%, 0.5%, or 0.05% of a given value or range.

BRIEF DESCRIPTION OF THE DRAWINGS

FIG. 1 shows the effect of CDN1001, CDN1054 and CDN1234 on IAEDANS-SERCA, indicated by fluorescence lifetime ($\tau_D$). Time-resolved fluorescence experiments were performed in the presence of DMSO (control) or 10 μM compound to detect modulation of SERCA by different test compounds. $\tau_D$ is increased by all compounds; CDN1054 is the most potent (18% increase).

FIGS. 2A-2B shows the effect of CDN1001, CDN1054 and CDN1234 on IAEDANS-SERCA/TNP-ADP, indicated by fluorescence lifetime ($\tau_D$) (A) and time-resolved FRET (B). Time-resolved fluorescence experiments were performed in the presence of DMSO (control) or 10 μM compound to detect modulation of SERCA by different test compounds. All compounds increase FRET, corresponding to a decrease in the distance R between N and P domains.

FIG. 3 shows the dose response effect of CDN1054 on IAEDANS-SERCA in the presence and absence of TNP-ADP, indicated by fluorescence lifetime ($\tau_D$). CDN1054 increases the donor lifetime $\tau_D$ and slightly decreases $\tau_{DA}$.

FIG. 4 shows the dose response effect of CDN1054 on IAEDANS-SERCA in the presence and absence of TNP-ADP, indicated by time-resolved FRET. CDN1054 increases FRET. This corresponds to a decrease in the distance R between N and P domains, by several angstroms.

DETAILED DESCRIPTION

Provided herein are methods for identifying molecules capable of modulating SERCA, the SERCA-PLB complex or the microenvironment of the complex. An exemplary assay provided herein is FRET. Also provided herein are FRET assays that are optimized for HTS for identifying molecules that modulate SERCA, the SERCA-PLB complex or the microenvironment of the complex, in the presence or absence of a membrane. Further provided are kits for carrying out said methods for identifying molecules.

A. SERCA

Without being bound by any theory, SERCA belongs to the cluster of ATP-driven ion-motive ATPases. SERCA is a regulator of calcium transport. Several different isoforms of SERCA, SERCA1a, SERCA1b, SERCA2a, SERCA2b and SERCA3, are known in vertebrates. SERCA1 is expressed in fast-twitch skeletal muscle fibers, whereas SERCA2 is expressed in muscle and non-muscle cells. Slow-twitch skeletal and cardiac muscle only express SERCA2a, while SERCA2b is expressed in all non-muscle tissue. (Toyofuku et al., (1993) *J. Biol. Chem.* 268:2809-2815).

Without being bound by any theory, modulation of SERCA may have an effect on the formation or properties (e.g., conformation or binding affinity between SERCA and PLB) of SERCA-PLB complex. In certain embodiments, the compound modulates the SERCA-PLB complex or its microenvironment through modulating the SERCA. In certain embodiments, the compound modulates SERCA through direct binding to SERCA. In one embodiment, the compound modulates the secondary structure of the SERCA. In another embodiment, the compound modulates the tertiary structure of the SERCA. In yet another embodiment, the compound activates the SERCA. In yet another embodiment, the compound inhibits the SERCA.

Without being bound by any theory, the X-ray crystallographic studies revealed the overall architecture of SERCA. Based on the crystal structure, SERCA has four functional domains: the nucleotide-binding (N), phosphorylation (P), actuator (A), and transmembrane (TM) domains. (Toyoshima et al., (2004) *Annu. Rev. Biochem.* 73:269-292). The P, N and A domains reside on the cytoplasmic face of SERCA: the P and N domains form the catalytic site of SERCA, whereas the A domain is involved in the transmission of major conformational changes. The conformation of SERCA (e.g., the interdomain distance of SERCA) has been shown to respond to modulation of small molecules. For example, upon calcium binding, the N and A domains of SERCA have been shown to move apart from each other by several nanometers (Winters et al., (2008) Biochemistry 47:4246-4256).

SERCA as used herein can be WT-SERCA or a SERCA derivative, and may comprise one or more of the SERCA isoforms. In certain embodiments of the methods and kits provided herein, the SERCA is WT-SERCA. In certain embodiments, the SERCA is a SERCA derivative. In certain embodiments, the SERCA is SERCA1a, SERCA1b, SERCA2a, SERCA2b, SERCA3, or a combination thereof.

SERCA as used herein can be chemically synthesized or purified from cells, and may be naturally occurring or engineered into the cell (e.g., recombinantly produced). The cells may be prokaryotic or eukaryotic. The cells may also be taken from an animal tissue, and the tissue may be taken from a body part.

In certain embodiments of the methods and kits provided herein, SERCA is synthetic. In certain embodiments, SERCA is naturally occurring. In certain embodiments, SERCA is engineered into the cell (e.g., recombinantly produced). In certain embodiments, SERCA is purified from crude SR. In certain embodiments, the crude SR is purified from cells. In certain embodiments, SERCA is purified from cells or viruses expressing SERCA. In certain embodiments, the cells are prokaryotic cells expressing SERCA (e.g., *Escherichia coli*) In certain embodiments, the cells are eukaryotic cell lines expressing SERCA (e.g., insect or mammalian cells). In certain embodiments, the cells are prepared from an animal tissue. The animal tissue can be a dissected tissue, microdissected tissue, a tissue subregion or a tissue biopsy sample. Examples of animal tissues include, but are not limited to, tissues taken from invertebrates such as *Caenorhabditis elegans* or from vertebrates such as such as reptiles, birds and mammals (e.g., cows, pigs, horses, cats, dogs, rabbits, rats and human beings). In certain embodiments, the animal tissue is a muscle tissue. In certain embodiments, the muscle tissue is a cardiac muscle tissue, skeletal muscle tissue, smooth muscle tissue, or a combination thereof. In certain embodiments, the muscle tissue is prepared from a body part. The body part may be any in vivo or ex vivo body part. In certain embodiments, the body part is an in vivo body part such as brain, liver, heart, aorta, coronary artery, kidney, lung, spleen, retina, bone, lymph node, endocrine gland, reproductive organ, blood, nerve, vascular tissue and olfactory epithelium. In certain embodiments, the body part is an ex vivo body part such as an arm, a leg and the back. In certain embodiment, the body part is taken from a New Zealand white rabbit. In one embodiment, the body part is a leg taken from a New Zealand white rabbit. In another embodiment, the body part is the back taken from a New Zealand white rabbit. In yet another embodiment, the body part is a porcine muscle tissue.

B. PLB

Without being bound by any theory, PLB is a regulator of SERCA-mediated calcium transport in muscle and endothelial cells (Lindemann et al., (1983) *J. Biol. Chem.* 258:464-471; Hoh (1992) *Current Opinion in Rheumatology,* 4:801-808; Sutliff et al., (1999) *Circ. Res.* 84(3):360-4). PLB is most abundantly expressed in heart ventricles and at much lower levels in atrial or slow twitch muscle (Jones & Field (1993) JBC 258, 11486. PLB is expressed in mouse aorta (Lalli et al., (1997) *Circ. Res.* 80(4): 506-513) and it is contemplated that PLB controls SERCA in peripheral vascular tissue. Through its inhibitory effects on the SERCA present in the cardiac tissue, PLB represses both the rates of relaxation and contraction in the mammalian heart.

Without being bound by any theory, several mutations in PLB have been studied, including loss-of-function mutations (e.g., S16E, L31A, L7A, R9E, I12A, N34A, I38A, L42A) and gain-of-function mutations (e.g., N27A, L37A, and I40A) (Trieber et al., (2005) *Biochemistry,* 44(9):3289-3297), where function refers to inhibition of SERCA. Some of these mutations have been shown to have an impact on PLB's inhibitory effect on SERCA. For example, mutation of I40A in PLB (I40A-PLB) has been shown to produce monomeric PLB, rather than the wild-type pentameric structure. The I40A-PLB mutant binds very tightly to SERCA and has a superinhibitory effect on SERCA; i.e., gain of function.

Without being bound by any theory, modulation of PLB may influence the formation or properties (e.g., conformation or binding affinity between SERCA and PLB) of SERCA-PLB complex. In certain embodiments, the compound modulates the SERCA-PLB complex or its microenvironment through modulating the PLB. In one embodiment, the compound modulates the secondary structure of the PLB. In another embodiment, the compound modulates the tertiary structure of the PLB. In yet another embodiment, the compound activates the PLB. In yet another embodiment, the compound inhibits the PLB.

PLB as used herein can be WT-PLB or a PLB derivative. In certain embodiments of the methods and kits provided herein, the PLB is WT-PLB. In certain other embodiments, the PLB is a PLB derivative. In certain embodiments, the PLB derivative comprises one or more of amino acid modifications relative to WT-PLB. In certain embodiments, the one or more of amino acid modifications are amino acid substitutions in PLB. In certain embodiments, the amino acid substitutions are one or more of substitution of serine to glutamate at position 16, substitution of leucine to alanine at position 31, substitution of cysteine to alanine at position 36, substitution of isoleucine to alanine at position 40, substitution of cysteine to phenylalanine at position 41. In certain embodiments, the amino acid substitution is a substitution of serine to glutamate at position 16. In certain embodiments, the amino acid substitution is a substitution of leucine to alanine at position 31. In certain embodiments, the amino acid substitution is a substitution of cysteine to alanine at position 46. In certain embodiments, the amino acid substitution is a substitution of isoleucine to alanine at position 40. In certain embodiments, the amino acid substitution is a substitution of cysteine to phenylalanine at position 41.

PLB as used herein may be chemically synthesized or purified from cells, and may be naturally occurring or engineered into the cell (e.g., recombinantly produced). The cells may be prokaryotic or eukaryotic. The cells may also be taken from an animal tissue, and the tissue may be taken from a body part.

In certain embodiments of the methods and kits provided herein, PLB is synthetic. In certain embodiments, PLB is naturally occurring. In certain embodiments, PLB is engineered into the cell (e.g., recombinantly produced). In certain embodiments, PLB is purified from crude SR. In certain embodiments, the crude SR is purified from cells. In certain embodiments, PLB is purified from cells or viruses expressing PLB. In certain embodiments, the cells are prokaryotic cells expressing PLB (e.g., *Escherichia coli*). In certain other embodiments, the cells are eukaryotic cell lines expressing PLB (e.g., insect or mammalian cells). In certain embodiments, the cells are Sf21/baculovirus cells. In certain embodiments, the cells are prepared from an animal tissue. The animal tissue can be a dissected tissue, microdissected tissue, a tissue subregion or a tissue biopsy sample. Examples of animal tissues include, but are not limited to, tissues taken from invertebrates such as *Caenorhabditis elegans* or from vertebrates such as reptiles, birds and mammals (e.g., cows, pigs, horses, cats, dogs, rabbits, rats and human beings). In certain embodiments, the animal tissue is a muscle tissue. In certain embodiments, the muscle tissue is a cardiac muscle tissue, skeletal muscle tissue, smooth muscle tissue, or a combination thereof. In certain embodiments, the muscle tissue is prepared from a body part. The body part may be any in vivo or ex vivo body part. In certain embodiments, the body part is an in vivo body part such as brain, liver, heart, aorta, coronary artery, kidney, lung, spleen, retina, bone, lymph node, endocrine gland, reproductive organ, blood, nerve, vascular tissue and olfactory epithelium. In certain embodiments, the body part is an ex vivo body part such as an arm, a leg and the back. In certain embodiments, the body part is taken from a rabbit. In certain embodiments, the body part is taken from a New Zealand white rabbit. In one embodiment, the body part is a leg taken from a New Zealand white rabbit. In another embodiment, the body part is the back taken from a New Zealand white rabbit. In yet another embodiment, the body part is a porcine muscle tissue.

In certain embodiments of the methods and kits provided herein, the PLB is chemically synthesized. In certain embodiments, the synthesis may be carried out by solid-phase synthesis such as on an Fmoc-Leu-PEG-PS resin (e.g., Example 3). In certain embodiments, the PLB which is chemically synthesized is acetylated. In certain embodiments, the PLB comprises one or more additional residues before the first residue, Met, at the N-terminus. In certain embodiments, the one or more additional residues are one or more of naturally occurring amino acids, Ala, Arg, Asn, Asp, Cyc, Gln, Glu, Gly, His, Ile, Leu, Lys, Met, Phe, Pro, Ser, Thr, Trp, Tyr and Val. In certain embodiments, the additional residue is Lys at position 0 before Met at position 1 of PLB.

The relative ratio SERCA to PLB is tested and optimized in the methods disclosed herein to obtain optimal detection signals and reproducibility of the assays.

In certain embodiments, the molar ratio of SERCA to PLB ranges from about 1 to 10 to about 10 to 1. In certain embodiments, the molar ratio of SERCA to PLB ranges from about 1 to 7 to about 7 to 1. In certain embodiments, the molar ratio of SERCA to PLB ranges from about 1 to 6 to about 6 to 1. In certain embodiments, the molar ratio of SERCA to PLB is about 5 to 1. In certain embodiments, the SERCA, when contacted with the PLB in the presence of a test compound and one or more lipids, is at a concentration ranging from about 1 nM to about 200 μM. In certain embodiments, the SERCA is at a concentration of about 90 nM. In certain embodiments, the PLB, when contacted with the SERCA in the presence of a test compound and one or more lipids, is at a concentration ranging from about 1 nM to about 200 μM. In certain embodiments, the PLB is at a concentration of about 450 nM.

C. FRET

FRET is an exemplary assay provided herein to identify test compounds which modulate SERCA or the interaction between SERCA and PLB. In FRET, a chromophore (donor) transfers, after excitation by a light source, its energy to another chromophore (acceptor). The energy transfer occurs when the emission spectrum of the donor overlaps significantly with the excitation spectrum of the acceptor. When the donor is excited, its emission is diminished or quenched due to resonance transfer of energy to the acceptor chromophore and the emission of the acceptor chromophore is enhanced.

Without being bound by any theory, the FRET rate k, which determines the FRET efficiency E according to $E=1/(1+k)$, is inversely proportional to the sixth power of the distance between the donor and the acceptor. The extreme sensitivity of the FRET process on the distance between molecules renders it a very useful tool for the resolution of intracellular protein arrangements and protein dynamics.

FRET described herein can be observed after the process has reached a steady state (e.g., steady-state FRET) or alternatively, in a time domain manner during the lifetime of the donor chromophore (e.g., time-resolved FRET).

1. Steady-State FRET

Without being bound by any theory, FRET efficiency can be calculated from the decrease of donor steady-state fluorescence ($F_D$) due to the presence of acceptor ($F_{DA}$), or from the average fluorescence lifetimes $\tau_D$ and $\tau_{DA}$, according to the following equation:

$$FRET=\left(1-\frac{F_{DA}}{F_D}\right)=\left(1-\frac{\tau_{DA}}{\tau_D}\right)$$

Without being bound by any theory, donor-acceptor distance R can be calculated from:

$$R=R_0(\mathrm{FRET}^{-1}-1)^{1/6}$$

2. Fluorescence Lifetime

The lifetime of the donor chromophore ($\tau$) upon excitation can be measured in the absence ($\tau_D$) or presence ($\tau_{DA}$) of the acceptor chromophore.

Without being bound by any theory, lifetimes of donor chromophore can be determined from time-resolved fluorescence, which can be analyzed as follows:

$$F(t)=F_0\sum_{i=1}^{n}x_i e^{-t/\tau i}$$

where $\tau_i$ and $x_i$ are the excited-state lifetimes and mole fractions, respectively. This function was convoluted with the instrument-response function and fit to the experimental data. $F_0$, $\tau_i$ and $x_i$ were varied to minimize $\chi^2$, increasing n until there was no significant decrease in $\chi^2$ with further increase in n. This typically resulted for n=3. Distance measurements assumed random orientation of fluorophores. This assumption is supported by the agreement of distance measurements with different donor-acceptor pairs.

3. Time-Resolved FRET

The time-resolved FRET as illustrated herein can be measured on a timescale suitable for detecting the dynamic change of the FRET process. In certain embodiments, the time-resolved FRET is measured on a timescale ranging from $10^{-3}$ to $10^{2}$ nanosecond, from $10^{-2}$ to 10 nanosecond, or from 0.1 to 1 nanosecond. In one embodiment, the time-resolved FRET is measured on a nanosecond timescale. In another embodiment, the time-resolved FRET is measured on a 0.1 nanosecond timescale. In certain embodiments, time-resolved FRET is measured over a time range of 0.1 to 100 nanosecond, with time resolution of 0.01 to 1 nanosecond per point.

4. Intramolecular Versus Intermolecular FRET

FRET as provided herein can be observed intramolecularly, for example, between two chromophores labeled within a single molecule (e.g., SERCA). In certain embodiments, intramolecular FRET in SERCA can be measured in the absence of any other molecules. In certain embodiments, intramolecular FRET in SERCA can be measured in the presence of one or more interacting proteins (e.g., PLB).

FRET as provided herein can also be detected intermolecularly, for example, between two chromophores labeled in two different molecules (e.g., in SERCA and PLB).

D. Chromophores

Any appropriately selected chromophores can be used as the donor-acceptor pairs in the FRET assay, provided that the emission spectrum of the donor overlaps with the excitation spectrum of the acceptor. Both the donor and acceptor can absorb light energy, but only the donor is required to emit light energy, i.e., the donor can be fluorescent and the acceptor can be non-fluorescent. If the acceptor is fluorescent, it is desirable to make use of a donor-acceptor pair in which the acceptor is not normally excited at the wavelength used to excite the donor. Furthermore, two identical chromophores can serve as donor and acceptor, in which case energy transfer is determined by measuring depolarization of fluorescence.

Non-limiting examples of suitable chromophores for FRET assays disclosed herein are those suitable for analysis by conventional flow cytometry. FRET pairs which can be used for detection by most conventional flow cytometers are discussed in, for example, Szollosi et al. (1998) *Communications in Clinical Cytometry*, pp. 159-179, vol. 34. Chromophores as used herein may be fluorescent or non-fluorescent (e.g., luminescent components, or 4-((4-(dimethylamino)phenyl)azo)benzoic acid (DABCYL)). In certain embodiments, combinations of chromophores as used herein comprise those used in the classical tandem conjugates (see U.S. Pat. No. 7,413,862).

Examples of fluorescent components that are suitable for FRET assays disclosed herein include, but are not limited to, fluorescein, rhodamine, 4-nitrobenzo-2-oxa-1,3-diazole (NBD); cascade blue, 4,4-difluoro-5,7-diphenyl-4-bora-3a,4a-diaza-s-indacene-3-propionic acid; 4,4-difluoro-5,p-methoxyphenyl-4-bora-3a,4a-diaza-s-indacene-3-propionic acid; 4,4-difluoro-5-styryl-4-bora-3a,4a-diaza-s-indacene-propionic acid; 6-carboxy-X-rhodamine, N,N,N',N'-tetramethyl-6-carboxyrhodamine; iodoacetyl-directed probes such as 5-((((2-iodoacetyl)amino)ethyl)amino)naphthalene-1-sulfonic acid (IAEDANS, used interchangeably with AEDANS); 5-carboxyfluorescein; 6-carboxyfluorescein; 6-(fluorescein-5-carboxamide)hexanoic acid; fluorescein isothiocyanate (FITC); tetramethylrhodamine isothiocyanate (TRITC); Texas Red (TR); eosin; a phycobiliprotein; cyanine dye; coumarin; R-phycoerythrin; allophycoerythrin (APC); a R-phycoerythrin (R-PE) conjugate; a Alexa Fluor dye; a quantum dot dye; maleimide-directed probes such as 4-dimethylaminoazobenzne-4'-maleimide (DABmal) and fluorescein-5-maleimide (Fmal); or a combination thereof (e.g., tandem conjugates).

In certain embodiments, chromophores used herein are nucleotide analogs such as ATP-, ADP- or AMP-analogs (see, e.g., Bagshaw (2001) *J. of Cell Science* 114:459-460). In certain embodiments, the nucleotide analogs are fluorescent. Examples of fluorescent nucleotide analogs include, by way of illustration, 2'-(or-3')-O-(trinitrophenyl)adenosine 5'-triphosphate (TNP-ATP), 2'-(or-3')-O-(trinitrophenyl)adenosine 5'-diphosphate (TNP-ADP), e-ATP, e-aza-ATP, FTP, 2AP-TP, ant-ATP. Mant-ATP, DEDA-ATP, FEDA-ATP, REDA-ATP and Cys3-EDA-ATP. Exemplary structures of representative nucleotide analogs are shown below.

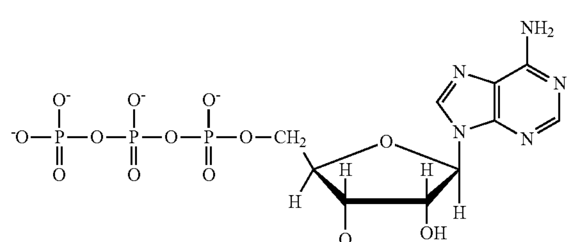

TNP-ATP

TNP-ADP e-ATP

-continued

FTP

2AP-TP ant-ATP

Mant-ATP

-continued
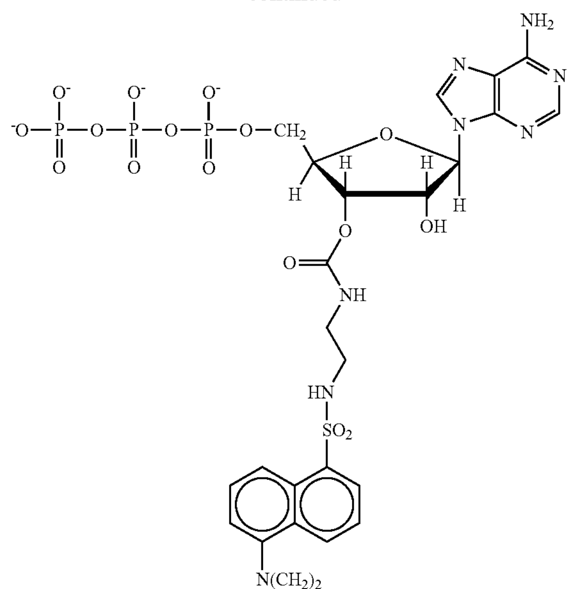
DEDA-ATP
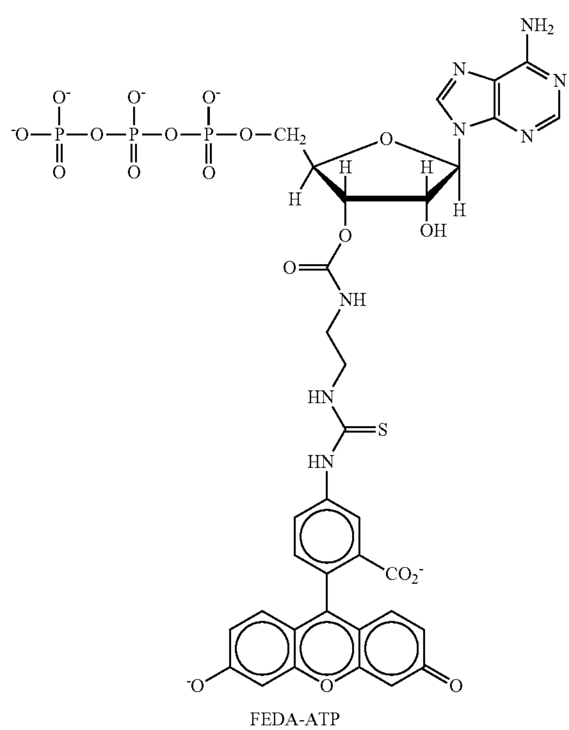
FEDA-ATP
-continued
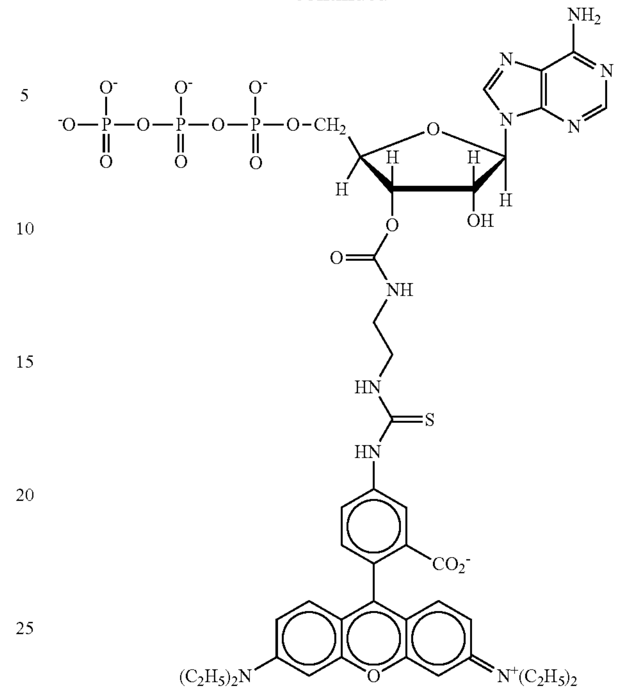
REDA-ATP
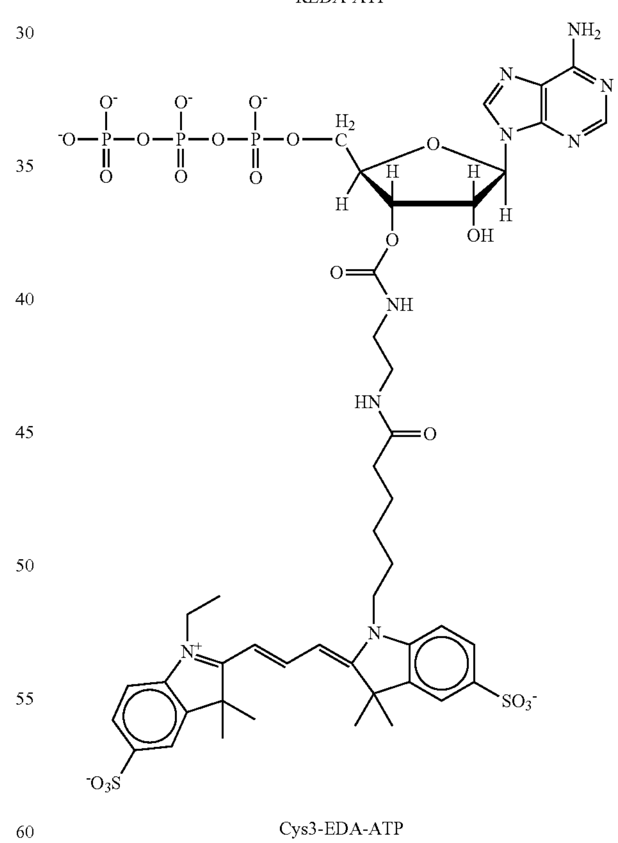
Cys3-EDA-ATP
Non-limiting examples of luminescent components that are suitable for FRET assays disclosed herein include, but are not limited to, the luminescent ions of europium and terbium introduced as lanthanide chelates (Thomas et al., (1978) *Proc Natl Acad Sci USA,* 75: 5746-5750).

Non-limiting examples of donor-acceptor pairs include fluorescein and rhodamine, NBD and rhodamine, NBD and eosin, NBD and erythrosine, fluorescein and eosin, fluorescein and erythrosin, dansyl and rhodamine, acridine orange and rhodamine, lanthanide ion and fluorescein, IAEDANS and TNP-ADP, IAEDANS and FITC, IAEDANS and DABmal, IAEDANS and Fmal, and IAEDANS and DABCYL. In one embodiment, the donor and acceptor pair as used herein is IAEDANS and TNP-ADP.

1. Chromophore Labeling for Intramolecular FRET

Labeling of SERCA with a first chromophore at a first position can be performed by any methods known in the art (e.g., Mueller et al., (2004) *Biochemistry* 43:8754-8765, Example 3). The first chromophore can be labeled at any locations in SERCA. In certain embodiments, the first chromophore is labeled in one of the functional domains of SERCA: the nucleotide-binding (N) domain, the phosphorylation (P) domain, the actuator (A) domain and the transmembrane (TM) domain.

In certain embodiments, SERCA is further labeled with a second chromophore at a second position different from the first position for intramolecular FRET detection, wherein the first and the second chromophores can be used for energy transfer. In certain embodiments, the second chromophore is labeled in N, P, A or TM domain in SERCA. In certain embodiments, either the first or the second chromophore is labeled on the N-terminus of SERCA. In certain embodiments, both the first and the second chromophores are labeled on the N-terminus of SERCA. In certain embodiments, either the first or the second chromophore is labeled on the C-terminus of SERCA. In certain embodiments, both the first and the second chromophores are labeled on the C-terminus of SERCA. In certain embodiments, the first and the second chromophores are labeled in the same domains of SERCA. In other embodiments, the first and the second chromophores are labeled in different domains of SERCA. In certain embodiments, the first and the second chromophores are labeled in N (or P) and P (or N) domains, respectively. In certain embodiments, the first and the second chromophores are labeled in A (or P) and P (or A) domains, respectively. In certain embodiments, the first and the second chromophores are labeled in A (or N) and N (or A) domains, respectively. In certain embodiments, the first and the second chromophores are labeled in TM (or A) and A (or TM) domains, respectively. In certain embodiments, the first and the second chromophores are labeled in TM (or N) and N (or TM) domains, respectively. In certain embodiments, the first and the second chromophores are labeled in TM (or P) and P (or TM) domains, respectively.

In certain embodiments, one of the first and the second chromophores is covalently bound to SERCA. In certain embodiments, both the first and the second chromophores are covalently bound to SERCA. In certain embodiments, either the first or the second chromophore is non-covalently bound to SERCA, for example, through hydrogen bonds, ionic bonds, Van der Waals forces, and hydrophobic interactions. In certain embodiments, both the first and the second chromophores are non-covalently bound to SERCA, for example, through hydrogen bonds, ionic bonds, Van der Waals forces, and hydrophobic interactions. In certain embodiments, the first chromophore is covalently bound to SERCA while the second chromophore is non-covalently bound to SERCA. In certain embodiments, the first chromophore is non-covalently bound to SERCA while the second chromophore is covalently bound to SERCA.

In certain embodiments, either the first or the second chromophores is labeled on a cysteine residue in SERCA. In certain embodiments, the first and the second chromophores are each labeled on a cysteine residue in SERCA. In certain embodiments, the cysteine residue is at position 344, 364, 670 or 674 in SERCA. In certain embodiments, either the first or the second chromophores is labeled on the side chain of a lysine residue. In certain embodiments, the first and the second chromophores are each labeled on the side chain of a lysine residue. In certain embodiments, either the first or the second chromophores is labeled on the main chain of a lysine residue. In certain embodiments, the first and the second chromophores are each labeled on the main chain of a lysine residue. In certain embodiments, the lysine residue is at position 515 in SERCA.

In certain embodiments of methods and kits provided herein, the first chromophore is an acceptor, and the second chromophore is a donor. In certain embodiments, the first chromophore is a donor, and the second chromophore is an acceptor. In certain embodiments, the first or the second chromophores is a fluorescent component. In certain embodiments, both the first and the second chromophores are a fluorescent component. In certain embodiments, the first or the second chromophores is a non-fluorescent component. In certain embodiments, both the first and the second chromophores are a non-fluorescent component. In certain embodiments, the fluorescent component is IAEDANS. In certain embodiments, the non-fluorescent component is DABCYL. IAEDANS as used herein can be any forms or derivatives of IAEDANS. DABCYL as used herein can be any forms or derivatives of DABCYL, including, but not limited to, the amino-reactive form of DABCYL (e.g., DABCYL, succinimidyl ester (DABCYL, SE)). In certain embodiments, the first chromophore is IAEDANS and the second chromophore is TNPADP.

2. Chromophore Labeling for Intermolecular FRET

For intermolecular FRET, labeling of SERCA and PLB with a first and second chromophores, respectively, may be performed, for example, by the procedure described in Mueller et al., (2004) *Biochemistry* 43:8754-8765 (e.g., Examples 3 and 5). The first and the second chromophores can be labeled at any locations in SERCA and PLB. In certain embodiments of the methods and kits provided herein, the first chromophore is labeled on the N-terminus of SERCA. In certain embodiments, the first chromophore is labeled on the C-terminus of SERCA. In certain embodiments, the first chromophore is labeled in the N, P, A or TM domain in SERCA. In certain embodiments, the first chromophore is labeled on a cysteine residue in SERCA. In certain embodiments, the cysteine residue is at position 344, 364, 670 or 674 in SERCA. In certain embodiments, the first chromophore is labeled on a lysine residue in SERCA. In certain embodiments, the lysine residue is at position 515 in SERCA. In certain embodiments, the first chromophore is labeled on the side chain of the lysine residue. In certain embodiments, the first chromophore is labeled on the main chain of the lysine residue.

In certain embodiments, the second chromophore is labeled on the N-terminus of PLB. In certain embodiments, the second chromophore is labeled on the C-terminus of PLB. In certain embodiments, the second chromophore is labeled on a lysine residue in PLB. In certain embodiments, the lysine residue is at position 0 in PLB. In certain embodiments, the lysine residue is at position 3 in PLB. In certain embodiments, the second chromophore is labeled on the side chain of the lysine residue. In certain embodiments, the second chromophore is labeled on the main chain of the lysine residue.

In certain embodiments, the first chromophore is covalently bound to SERCA. In certain embodiments, the first chromophore is non-covalently bound to SERCA, for example, through hydrogen bonds, ionic bonds, Van der Waals forces, and hydrophobic interactions. In certain embodiments, the second chromophore is covalently bound to PLB. In certain embodiments, the second chromophores is non-covalently bound to PLB, for example, through hydrogen bonds, ionic bonds, Van der Waals forces, and hydrophobic interactions.

In certain embodiments of methods and kits provided herein, the first chromophore is a fluorescent component. In certain embodiments, the second chromophore is a fluorescent component. In certain embodiments, the second chromophore is a non-fluorescent component. In certain embodiments, the fluorescent component is IAEDANS. In certain embodiments, the non-fluorescent component is DABCYL. In certain embodiments, the first chromophore is an acceptor, and the second chromophore is a donor. In certain embodiments, the first chromophore is a donor, and the second chromophore is an acceptor. In certain embodiments, SERCA is labeled with IAEDANS and PLB is labeled with DABCYL. IAEDANS as used herein can be any forms or derivatives of IAEDANS. DABCYL as used herein can be any forms or derivatives of DABCYL, including, but not limited to, the amino-reactive form of DABCYL (e.g., DABCYL, succinimidyl ester (DABCYL, SE)).

In certain embodiments of methods and kits provided herein, SERCA is labeled with an acceptor and PLB is labeled with a donor. In certain embodiments, SERCA is labeled with a donor and PLB is labeled with an acceptor.

E. Methods

In certain embodiments, provided herein are methods for identifying a compound that modulates SERCA, comprising: (a) providing SERCA labeled with a first chromophore at a first position; (b) exciting the chromophore; and (c) measuring the fluorescence lifetime of the first chromophore; wherein a difference between the fluorescence lifetime in the presence of the test compound and the fluorescence lifetime in the absence of the test compound indicates that the test compound modulates SERCA, such that the fluorescence lifetime of the chromophore is altered. In one embodiment, the SERCA is further labeled with a second chromophore at a second position, wherein the second position is different from the first position, and wherein the chromophores can be used for energy transfer.

In certain embodiments, provided herein are methods for identifying a compound that modulates SERCA, comprising: (a) providing SERCA labeled with a first chromophore at a first position and a second chromophore at a second position, wherein the second position is different from the first position, and wherein the first and the second chromophores can be used for energy transfer; (b) exciting either the first or the second chromophore; and (c) measuring FRET between the chromophores; wherein a difference between FRET in the presence of the test compound and FRET in the absence of the test compound indicates that the test compound modulates SERCA, such that the energy transfer between the two chromophores is altered.

In certain embodiments, provided herein are methods for identifying a compound that modulates the SERCA-PLB complex or its microenvironment, comprising: (a) providing SERCA labeled with a first chromophore; (b) providing PLB labeled with a second chromophore, wherein the PLB is WT-PLB or a PLB derivative that gives a FRET potency suitable for HTS, and wherein the chromophores can be used for energy transfer; (c) contacting the SERCA of step (a) with the PLB of step (b) in the presence of a test compound and one or more lipids; (d) exciting either the first or the second chromophore; and (e) measuring FRET between the chromophores; wherein a difference between FRET in the presence of the test compound and FRET in the absence of the test compound indicates that the test compound modulates the SERCA-PLB complex or its microenvironment, such that the energy transfer between the two chromophores is altered.

Perturbed or disrupted interactions between SERCA and PLB (e.g., due to congenital mutations in PLB) have shown to affect the formation of SERCA-PLB complex. In certain embodiments of the methods provided herein, the compound modulates the SERCA-PLB complex through modulating the interaction between SERCA and PLB. In certain embodiments, the SERCA-PLB interactions can be disrupted, for example, by a compound that modulates the SERCA-PLB complex.

Modulation of SERCA may have an effect on the formation or properties (e.g., conformation or binding affinity between SERCA and PLB) of SERCA-PLB complex. In certain embodiments, the compound modulates the SERCA-PLB complex or its microenvironment through modulating the SERCA. In one embodiment, the compound modulates the secondary structure of the SERCA. In another embodiment, the compound modulates the tertiary structure of the SERCA. In yet another embodiment, the compound activates the SERCA. In yet another embodiment, the compound inhibits the SERCA.

Modulation of PLB may influence the formation or properties (e.g., conformation or binding affinity between SERCA and PLB) of SERCA-PLB complex. In certain embodiments, the compound modulates the SERCA-PLB complex or its microenvironment through modulating the PLB. In one embodiment, the compound modulates the secondary structure of the PLB. In another embodiment, the compound modulates the tertiary structure of the PLB. In yet another embodiment, the compound activates the PLB. In yet another embodiment, the compound inhibits the PLB.

Modulation of the microenvironment surrounding the SERCA-PLB complex (e.g., within several nanometers of the SERCA-PLB complex) in the absence of modulating the SERCA-PLB complex can affect the energy transfer between chromophores attached to the SERCA and PLB in a FRET assay setting. In certain embodiments, the methods provided herein can identify compounds that modulate the microenvironment of the SERCA-PLB complex. In certain embodiments, modulation of the microenvironment comprise modulating one or more of the components of the microenvironment. Such components include, but are not limited to, buffer, water, solvent and lipids. In certain embodiments, modulation of the microenvironment comprises modulating the lipids.

In certain embodiments, the methods provided herein are performed in the presence of calcium ions. In certain embodiments, the calcium ion concentration ranges from 10 nM to 200 μM. In certain embodiments, the calcium ion concentration ranges from 50 nM to 150 μM. In certain embodiments, the calcium ion concentration ranges from 1 μM to 100 μM.

F. FRET in a Membrane

Due to the complicated nature of membrane proteins, it is difficult to use standard methods of protein study, such as x-ray crystallography or NMR to study proteins incorporated into lipid bilayers. In certain embodiments, the methods provided herein are performed in the presence of one or more lipids and/or solvents in addition to the test compound.

Modulation of lipids in the absence of changes in SERCA and/or PLB activities and/or conformations may affect the microenvironment in which formation of the SERCA-PLB complex takes place. Therefore, in certain embodiments, the compound modulates the SERCA-PLB complex or its microenvironment through modulating the lipids.

To reconstitute the membrane system where SERCA and PLB interact in vivo and to optimize the dynamic range of the assays, the compositions of lipids and optionally, solvents are optimized in the methods disclosed herein.

Lipids suitable for methods and kits provided herein may be any lipids or a combination thereof in various ratios capable of forming a membrane known in the art. In certain embodiments, the lipids are naturally occurring. In certain embodiments, the lipids are synthetic. In certain embodiments, the lipids are one or more of fatty acyls, glycerolipids, glycerophospholipids, sphingolipids, saccharolipids, polyketides, sterol lipids, prenol lipids and a derivative thereof. In certain embodiments, the lipids are one or more of choline-based lipids (e.g., phosphatidylcholine (PC)), ethanolamine-based lipids (e.g., phosphatidylethanolamine (PE)), serine-based lipids (e.g., phosphatidylserine), glycerol-based lipids (e.g., phosphatidylglycerol), cholesterol-based lipids, dolichols, sphingolipids (e.g., sphingosine, gangliosides, or phytosphingosine), inositol-based lipids (e.g., phosphatidylinositol), cardiolipin, phosphatidic acid, lysophosphatides (e.g., lysophosphatides), hydrogenated phospholipids and a derivative thereof.

In certain embodiments, the lipids are one or more of PC, dioleoylphosphatidylcholine (DOPC), dimyristoylphosphatidylcholine (DMPC), dipalmitoylphosphatidylcholine (DPPC), distearoylphosphatidylcholine (DSPC), palmitoyl oleoylphosphatidylcholine (POPC), 2-dioleoyl-3-succinyl-sn-glycerol choline ester (DOSC), PE, dioleoylphosphatidylethanolamine (DOPE), dimyristoylphosphatidylethanolamine (DMPE), dipalmitoylphisphatidylethanolamine (DPPE), dioleoylphosphatidylserine (DOPS), dipalmitoylphosphatidylserine (DPPS), dioleoylphosphatidylglycerol (DOPG), dipalmitoylphosphatidylglycerol (DPPG), sphingomyelin (SM), sodium dodecyl sulphate (SDS), cholesterol (CHOL), cholesterol hemisuccinate (CHEMS), cholesterol-(3-imidazol-1-yl propyl)carbamate (CHIM), diacylglycerol hemisuccinate (DG-Succ), cholesterol sulphate (Chol-$SO_4$), dimethyldioctadecylammonium bromide (DDAB), dioleoylphosphatidic acid (DOPA), 1,2-dioleoyloxypropyl-3-dimethylhydroxyethylammonium chloride (DORI), 11,2-dioleoyl-3-trimethylammonium propane (DOTAP), N-(1-(2,3-dioleoyloxy)-propyl)-N,N,N-triethylammonium chloride (DOTMA), 1,2-dimyristyloxypropyl-3-dimethylhydroxyethylammonium bromide (DMRIE),1,2-dioleoyl-3-dimethylammonium propane (DODAP), N,N-dioleyl-N,N-dimethylammonium chloride (DODAC), 1,2-dioleoyl-3-dimethyl-hydroxyethylammonium bromide (DORIE), N-(1-(2,3-dioleyloxy)-propyl)-N-(2-(sperminecarboxamido)ethyl)-N,N-dimethylammonium trifluoroacetate (DOSPA), 1-(2-(oleoyloxy)ethyl)-2-oleyl-3-(2-hydroxyethyl)imidazolinium chloride (DOTIM), N-(trimethylammonioacetyl)-didodecyl-D-glutamate chloride (TMAG), N,N-di-n-hexadecyl-N,N dihydroxyethylammoniumbromide (DHMHAC), N,N-di-n-hexadecyl-N-methyl-N-(2-hydroxyethyl)ammonium chloride (DHDEAB), N,N-myristoyl-N-(1-hydroxyprop-2-yl)-N-methylammoniumchloride (DMHMAC), 1,2-dioleoyl-3-(4'-trimethylammonio)butanoyl-sn-glycerol (DOTB), Synthetic Amphiphiles Interdisciplinary (SAINT lipids), 4,(2,3-bis-acyloxy-propyl)-1-methyl-1H-imidazole (DOIM), 2,3-bis-palmitoyl-propyl-pyridin-4-yl-amine (DPAPy), 3β-(N—(N9,N9-dimethylaminoethane)carbamoyl)cholesterol (DC-Chol), 3β-(N—(N9,N9-trimethylaminoethane)carbamoyl) cholesterol (TC-Chol), 3β(N—(N,N'-Dimethylaminoethan)-carbamoyl)cholesterol (DAC-Chol), cetyltrimethylammonium bromide (CTAB), cationic cardiolipins (e.g. (1,3-bis-(1,2-bis-tetradecyloxy-propyl-3-dimethylethoxyammoniumbromide)-propane-2-ol) (NeoPhectin™), N-histidinyl-cholesterol hemisuccinate (HistChol), 4-(2-aminoethyl)-morpholino-cholesterol hemisuccinate (MoChol), histaminyl-cholesterol hemisuccinate (HisChol), and a derivative thereof.

In certain embodiments of the methods and kits disclosed herein, the lipids are one or more of PC, DOPC, DMPC, DPPC, DSPC, POPC, DOSC, PE, DOPE, DMPE, DPPE and a derivative thereof.

In certain embodiments of the methods and kits disclosed herein, the lipids are one or more of PC, DOPC, DMPC, DPPC, DSPC, POPC, DOSC and a derivative thereof.

In certain embodiments of the methods and kits disclosed herein, the lipids are one or more of PE, DOPE, DMPE, DPPE and a derivative thereof.

In certain embodiments of the methods and kits disclosed herein, the lipids are DOPC and DOPE. In certain embodiments, the weight ratio of DOPC to DOPE is from about 10 to 1 to about 1 to 10. In certain embodiments, the weight ratio of DOPC to DOPE is about 4 to 1.

Solvents suitable for methods and kits provided herein may be any solvent capable of facilitating lipid solubilization known in the art. In certain embodiments, the solvent is one or more of methanol, ethanol, acetonitrile and chloroform. In one embodiment, the solvent is methanol. In another embodiment, the solvent is ethanol. In yet another embodiment, the solvent is acetonitrile. In yet another embodiment, the solvent is chloroform. In certain embodiments, the solvent is an aqueous solution comprising one or more amphiphilic detergents. Examples of such detergents include, but are not limited to, oxylglucoside, octaethylene glycol monododecyl ether ($C_{12}E_8$), dodecylphosphocholine and deoxycholate.

Moreover, the relative ratio of lipid to SERCA and PLB are optimized in the methods disclosed herein. In certain embodiments, the molar ratio of lipids to SERCA ranges from about 100 to 1 and above. In certain embodiments, the molar ratio of lipids to SERCA ranges from about 200 to 1 to about 6000 to 1. In certain embodiments, the molar ratio of lipids to SERCA ranges from about 250 to 1 to about 5000 to 1. In certain embodiments, the molar ratio of lipids to SERCA is from about 300 to 1 to about 3000 to 1. the molar ratio of lipids to SERCA is from about 600 to 1 to about 1500 to 1. In certain embodiments, the molar ratio of lipids to SERCA is about 700 to 1.

In certain embodiments, the molar ratio of lipids to PLB ranges from about 10 to 1 to about 10000 to 1. In certain embodiments, the molar ratio of lipids to PLB ranges from about 50 to 1 to about 1500 to 1. In certain embodiments, the molar ratio of lipids to PLB ranges from about 90 to 1 to about 1000 to 1. In certain embodiments, the molar ratio of lipids to PLB ranges from about 110 to 1 to about 500 to 1. In certain embodiments, the molar ratio of lipids to PLB is about 120 to 1.

In certain embodiments, the molar ratio of SERCA to PLB is from about 1 to 10 to about 10 to 1. In certain embodiments, the molar ratio of SERCA to PLB is from about 1 to 7 to about 7 to 1. In certain embodiments, the molar ratio of SERCA to PLB is from about 1 to 6 to about 6 to 1. In certain embodiments, the molar ratio of SERCA to PLB is about 5 to 1. In certain embodiments of the methods provided herein, the SERCA of step (c) is at a concentration from about 1 nM to about 200 μM. In certain embodiments of the methods provided herein, the SERCA of step (c) is at a concentration of about 90 nM. In certain embodiments of the methods provided herein, the PLB of step (c) is at a concentration from about 1 nM to about 200 μM. In certain embodiments, the PLB of step (c) is at a concentration of about 450 nM.

In certain embodiments, the molar ratio of lipids to PLB to SERCA is about 100-6000 to 1-10 to 1-10. In certain embodiments, the molar ratio of lipids to PLB to SERCA is about 300-3000 to 2-8 to 1-6. In certain embodiments, the molar ratio of lipids to the PLB to SERCA is about 400-1200 to 3-7 to 1-5. In certain embodiments, the molar ratio of lipids to PLB to SERCA is about 500-800 to 4-6 to 1-3. In certain embodiments, the molar ratio of lipids to PLB to SERCA is about 700 to 5 to 1.

G. HTS

In certain embodiments, provided are kits for carrying out methods disclosed herein, in a container, and instructions for use.

In certain embodiments, provided herein are kits for identifying a compound that modulates the SERCA-PLB complex or its microenvironment, comprising: (a) SERCA labeled with a first chromophore; and (b) PLB labeled with a second chromophore; wherein the PLB is WT-PLB or a PLB derivative that gives a FRET potency suitable for HTS, and wherein the chromophores can be used for energy transfer.

In certain embodiments, provided are kits for identifying a compound that modulates the SERCA-PLB complex or its microenvironment, comprising: (a) a first oligonucleotide expressing SERCA; (b) a second oligonucleotide expressing PLB, and (c) a first and a second chromophore provided for labeling, wherein the PLB is WT-PLB or a PLB derivative that gives a FRET potency suitable for HTS, and wherein the chromophores can be used for energy transfer.

Due to the complexity of membrane proteins compared to soluble proteins, it has been very difficult to reconstitute a synthetic system that recapitulates the cellular environment in which SERCA and PLB interact in a large-scale reproducible manner. Moreover, observation of modulated SERCA-PLB complex or its microenvironment has been limited, for example, by unsuitable FRET potency or strong SERCA and PLB interactions that cannot be easily disrupted. Therefore, provided herein are methods and kits optimized for HTS.

For the HTS methods and kits provided herein, the suitable FRET potency is one which can be detected by introducing a perturbation to SERCA-PLB interaction (e.g., addition of a modulating compound). Therefore, in certain embodiments of the methods and kits provided herein, a suitable FRET potency is one that is within the dynamic range of the measuring instrument (e.g., fluorescence plate reader).

Without being bound by any theory, strong SERCA and PLB interactions that cannot be easily disrupted has limited the application of FRET assays to HTS. Therefore, in certain embodiments of the HTS methods and kits provided herein, the PLB is selected such that the interaction between SERCA and PLB can be disrupted. In certain embodiments, the SERCA-PLB interaction can be disrupted when the interaction is such that a range of test compounds give a range of results. In certain embodiments, the SERCA-PLB interaction can be disrupted if the binding affinity of SERCA to PLB is within one order of magnitude of that of SERCA to WT-PLB. In certain embodiments, the suitable binding affinity of SERCA to a PLB derivative is one with which the change in FRET due to the association and dissociation of SERCA and PLB can be detected by a measuring instrument. As such, in certain embodiments, the binding affinity of SERCA to PLB is one that is within the dynamic range of the measuring instrument.

Methods and kits disclosed herein may be carried out in numerous formats known in the art. In certain embodiments, the methods provided herein are carried out using solid-phase assay formats. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (e.g., round- or flat-bottom multi-well plates). Exemplary multi-well plate formats that can be used in the methods provided herein include those found on 96-well plates (12×8 array of wells), 384-well plates (24×16 array of wells), 1536-well plate (48×32 array of well), 3456-well plates and 9600-well plates. Other formats that may be used in the methods provided herein include, but are not limited to, single or multi-well plates comprising a plurality of domains. In certain embodiments, the plates are black-wall, black-bottom plates. In certain embodiments, the plates are black-wall, white-bottom plates. In certain embodiments, the plates have black walls and clear bottoms in order to allow bottom reading of the fluorescence signals. In certain embodiments, the plates are chosen with minimal and uniform intrinsic fluorescence intensity within the range utilized in the method to avoid interference with the FRET signals. In one embodiment, the plates do not emit signals between 420 nm and 600 nm. An exemplary commercially available plate that can be used for methods disclosed herein is NUNC 242764 (Thermo Fisher Scientific, Waltham, Mass.).

The methods provided herein, when carried out in standardized plate formats can take advantage of readily available equipment for storing and moving these plates as well as readily available equipment for rapidly dispensing liquids in and out of the plates (e.g., robotic dispenser, multi-well and multi-channel pipettes, plate washers and the like).

Detection of FRET may be carried out in numerous ways known in the field (see, e.g., U.S. Pat. No. 6,057,163). The signals may be read by any commercially available plate reader compatible with FRET assays. In certain embodiments, the plate reader is equipped with dual monochromators to allow spectrum acquisition (e.g., Gemini EM Fluorescence Microplate Reader, MDS Analytical Technologies). The FRET assays disclosed herein may be measured by any methods known in the art. In certain embodiments, the FRET assays disclosed herein are measured at a single emission wavelength. In certain embodiments, the entire emission spectrum of the FRET is measured. For example, when IAEDANS is the fluorescent donor, the emission wavelength is scanned from 420 nm to 600 nm. Analysis of the entire spectrum may minimize the fluorescence interference from test compounds, plates, and distortions from sample impurities. In certain embodiments, the plates in which the assays are carried out may be read from the top or by front-face illumination. In certain embodiments, the plates on which the assays are carried out are read from the bottom to allow a more robust separation of the fluorescence signal from light scattering in the membrane samples. Bottom reading is also necessary to avoid signal irregularities at the meniscus.

H. Test Compounds

The methods disclosed herein can be used for screening a plurality of test compounds. In certain embodiments, the plurality of test compounds comprises between 1 and 200,000 test compounds, between 1 and 100,000 test compounds, between 1 and 1,000 test compounds, between 1 and 100 test compounds, or between 1 and 10 test compounds. In certain embodiments, the test compounds are provided by compound libraries, whether commercially available or not, using combinatorial chemistry techniques. In certain embodiments, the compound libraries are immobilized on a solid support.

I. Kits

Kits for carrying out the methods provided herein are also contemplated. The kits provide useful tools for screening test compounds capable of modulating the SERCA-PLB complex or its microenvironment in a timely and consistent manner. The kits can be packaged in any suitable manner to aid research, clinical, and testing labs, typically with the various parts, in a suitable container along with instructions for use.

Provided herein are kits for identifying a compound that modulates the interaction between SERCA and PLB. In certain embodiments, the kits comprise (a) SERCA labeled with a first chromophore; and (b) PLB labeled with a second chromophore; wherein the PLB is WT-PLB or a PLB derivative that gives a FRET potency suitable for HTS, and wherein the chromophores can be used for energy transfer. In certain embodiments, the kits comprise (a) a first oligonucleotide expressing SERCA; (b) a second oligonucleotide expressing PLB; and (c) a first and a second chromophores provided for labeling, wherein the PLB is WT-PLB or a PLB derivative that gives a FRET potency suitable for HTS, and wherein the chromophores can be used for energy transfer. In certain embodiments, the kits may further comprise lipids and/or solvents. In certain embodiments, the interaction between SERCA and PLB can be disrupted. In certain embodiments, the kits may further comprise buffers and reagents needed for the procedure, and instructions for carrying out the assay. In certain embodiments, the kits may further comprise, where necessary, agents for reducing the background interference in a test, positive and negative control reagents, apparatus for conducting a test, and the like.

In certain embodiments of the methods and kits provided herein, solid phase supports are used for purifying proteins, labeling samples or carrying out the solid phase assays. Examples of solid phases suitable for carrying out the methods disclosed herein include beads, particles, colloids, single surfaces, tubes, multiwell plates, microtiter plates, slides, membranes, gels and electrodes. When the solid phase is a particulate material (e.g., beads), it is, in one embodiment, distributed in the wells of multi-well plates to allow for parallel processing of the solid phase supports.

It is noted that any combination of the above-listed embodiments, for example, with respect to SERCA and PLB samples, chromophores, solid support and the like, are also contemplated in relation to any of the various methods and/or kits provided herein.

The following examples are offered by way of illustration, and not by way of limitation.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); NMR (nuclear magnetic resonance); MALDI-TOF (Matrix-assisted laser desorption/ionization time-of-flight); BSA (bovine serum albumin); DMSO (dimethyl sulfoxide); sinapinic acid (3,5-dimethoxy-4-hydroxycinnamic acid); $MgCl_2$ (magnesium chloride); HBTU/HOBt/DIEA (2-(1H-benzotriazol-j-yl)-1,1,3,3,-tetramethyluronium hexafluorophosphate/N-Hydroxybenzotriazole/N-Ethyldiisopropylamine); DOPC (dioleoylphosphatidylcholine); DOPE (dioleoylphosphatidylethanolamine); KCl (potassium chloride); SDS (sodium dodecyl sulfate); NaOH (sodium hydroxide); TFA (trifluoracetic acid); and NEM (N-Ethylmaleimide).

Example 1

Preparation of Crude SR from Rabbit Skeletal Muscle

Crude SR was purified from skeletal muscle of New Zealand white rabbits. The rabbits were euthanized according to standard procedures recommended by the American Veterinary Medical Association and approved by the Institution's Animal Care and Use Committee on ice in a cold room (4° C.). The fast twitch skeletal muscle was removed from the back and leg and cut into 1 inch cubes. The muscle was then placed in a homogenizer at a ratio of 1 gram tissue/3 mL SR Buffer (20 mM MOPS, 0.1 M KCl, pH 7.0), blended, and centrifuged at 5,000 rpm in a Sorvall SLA-3000 Superlite rotor for 20 minutes. The supernatant was filtered and collected into a 2 L graduated cylinder. The remaining pellets were homogenized again and centrifuged at 5,000 rpm in a Sorvall SLA-3000 Superlite rotor for 30 minutes. The supernatants were then filtered and the filtrate was added to the previously collected supernatant. The filtered supernatant was centrifuged at 8,500 rpm in a Sorvall SLA-3000 Superlite rotor for 20 minutes to remove the mitochondria. Thereafter, the supernatant was filtered and 0.5M KCl was added to the filtrate to dissolve myosin for 10-15 minutes. The supernatant was centrifuged at 12,000 rpm Sorvall SLA-3000 Superlite rotor for 1 hour. The pellet was collected and resuspended with 100 mL Sucrose Buffer (20 mM MOPS, 0.3 M Sucrose, 1 mM $MaN_3$, pH 7.0). The resuspended pellet was subsequently centrifuged at 30,000 rpm in a Beckman Coulter Type 45 Ti rotor for 45 minutes. The pellet was then homogenized. The protein concentration was determined by Biuret assay with BSA as a standard. The resulting crude SR was divided into 4 mL aliquots in 10 mL freezer-proof tubes, flash frozen, and stored in <−60° C. freezer until used for purification.

Example 2

Preparation of Porcine Cardiac SR

The fresh porcine heart was placed into 10 mM (Sodium Bicarbonate Solution 10 mM Tris solution, pH 7.0 with Protease Inhibitors (10 mL/L of solution)) and transported to the lab. Protease Inhibitors contained 10 mL/L Aprotinin (0.1 mg/mL), Leupeptin (0.1 mg/mL), Benzamidine (80 mM), Pefbloc SC (100 mM) and Pepstatin A (0.1 mg/mL). The atria and fat was snipped off from the ventricles. Each ventricle was blended in the Sodium Bicarbonate Solution (about 5 mL/g of tissue) and centrifuged at 11,000×g for 20 minutes at 4° C. The supernatants were filtered through four layers of cheesecloth and stored on ice. The volume of the supernatant volume was measured. KCl was added to the supernatant for a final concentration of 0.6 M. The solution was stirred on ice for 1 hour and centrifuged at 100,000×g for 30 min, 4° C. The resulting pellet was resuspended in 10% sucrose solution with Protease Inhibitors. The solution was centrifuged at 100,000×g for 30 min, 4° C. The resulting pellet was resuspended in about 2 mL of 10% Sucrose Solution with Protease Inhibitors. The cardiac SR prep was aliquoted into microfuge tubes (500 μL/tube), flash frozen and stored at less than −60° C.

Example 3

SERCA Purification and Labeling

SERCA purification was performed in 0.01% $C_{12}E_8$ by the Reactive-Red method (Mueller et al., (2004) *Biochemistry* 43:8754-8765; Stokes et al., (1990) *Biophys. J.* 57:1-14). Briefly, crude SR obtained by procedure as described in Example 1 or 2 was added to reactive red resin type 3000CL with 8 mL 0.01% $C_{12}E_8$. The column was then washed with 300 mL double distilled water and stored in cold room overnight. 0.5 mg of lipid (sonicated DOPC and DOPE, 4:1 ratio by weight/mg protein) was added to the eluted sample, flash frozen and stored in liquid nitrogen. The protein concentration was determined by the Biuret method using BSA as the standard.

SERCA labeling was carried out essentially as described in Mueller et al., (2004) *Biochemistry* 43:8754-8765. Prior to labeling, the detergent was removed by the same method used in reconstitution as shown in Example 7. 18.2 μM SERCA was labeled with 273 μM IAEDANS in IAEDANS Labeling Buffer (80 mL KCl, 5 mM Mg $Cl_2$, 1 mM $CaCl_2$, 20 mM MOPS, pH 6.8) for 30 minutes at 25° C. in the dark. The free dye was then removed by centrifugation in a Ti45 rotor at 45,000 rpm for 30 minutes and wash three times with Wash Buffer (20 mM sucrose, 10 mM KCl, 20 mM MOPS, pH 7). The dye concentration was determined in labeled samples using an extinction coefficient of 6100 $M^{-1}$ $cm^{-1}$ at 334 nm after treatment with 1 mL 0.1 N NaOH and 1% SDS.

For intramolecular FRET detection, IAEDANS-labeled samples were subsequently incubated with TNP-ADP in the presence or absence of test compounds at various concentrations. Briefly, 1 μM of IAEDANS-SERCA was incubated with 30 μM of TNP-ADP in a buffer (50 mM KCl, 5 mM $MgCl_2$, 0.5 mM EGTA, 210 μM $CaCl_2$, 50 mM MOPS, pH 7.0) for 20 min at 25° C. The free dye was removed following the same procedure described above. The concentration of TNP-ADP was measured from its extinction coefficient 26.4 $mM^{-1}$ $cm^{-1}$ at 408 nm. The labeled SERCA proteins were flash-frozen and stored in the dark in liquid nitrogen until used for reconstitution and FRET measurements.

Example 4

Peptide Synthesis and Purification of PLB

Solid-phase synthesis of PLB peptide was essentially performed as described in Mueller et al., (2004) *Biochemistry* 43:8754-8765 and Karim et al., (2007) *Nature Protocols,* 2:43-49. In brief, the peptide was assembled on an Fmoc-Leu-PEG-PS resin by Fmoc chemistry using a PE Biosystems Pioneer peptide synthesis system. All couplings were performed in NMP, mediated by HBTU/HOBt/DIEA (4:4:8 (equivalent) with respect to peptide-resin. The N-terminal amino group was acetylated using acetic anhydride. An Fmoc removal step using 20% piperidine and 2% DBU in NMP is performed on 200 mg of peptide resin followed by treatment with 0.5 M acetic anhydride in 10 mL of DMF for 2 hours. Final deprotection was carried out by treatment with 2 mL freshly prepared Deprotection Solution (82.5% TFA, 5% phenol, 5% thioanisole, 2.5% 1,2 ethanedithiol, 5% water) for 6 hours at 25° C. The acetylated peptide resin was filtered, cleaved and washed with 2 mL of the Deprotection Solution. The combined filtrates were concentrated under nitrogen gas and precipitated in 30 mL of diethyl ether at 0° C. The precipitated peptide was collected by centrifugation and washed three times with diethyl ether.

Crude peptide was dissolved in 5 mL of TFA and purified by HPLC on a C-18 column equilibrated with 95% water, 2% acetonitrile and 3% 2-propanol. The peptide was eluted using a linear gradient to a final composition of 5% water, 2% acetonitrile, and 3% 2-propanol The fractions containing peptides were lyophilized. The final yield of purified PLB was approximately 26 mg (12% yield based on starting resin).

Example 5

Labeling of PLB with DABCYL-SE

Labeling of PLB was essentially performed following the procedure described in Mueller et al., (2004) *Biochemistry* 43:8754-8765. In short, 10 mg of acetylated, purified PLB peptide was dissolved at a concentration of 0.1 mM in 100 mM $NaHCO_3$ (pH 9.0) and 0.1% SDS. A 10-fold molar excess of DABCYL-SE was added from a 100 mM stock solution in DMF, and the sample was incubated for 16 hours at 25° C. on a shaker. Unreacted DABCYL-SE was removed by HPLC on a diphenyl column (Vydac, 219TP510; 5 μm, 300, 10×250 mm). DABCYL-labeled WT-PLB (DAB-I40A-PLB) was then eluted in a 30 minute, 0-100% A to B gradient with a 2.5 mL/minute flow rate (Buffer A, 95% water, 2% acetonitrile, 3% 2-propanol and 0.1% TFA; Buffer B, 5% water, 38% acetonitrile, 57% 2-propanol, and 0.1% TFA). The elution time was approximately 22-25 minutes. The fractions containing the peptide were lyophilized. Approximately 6.3 mg of DAB-WT-PLB was yielded. The dye concentration in labeled samples was determined by direct sample absorbance in methanol at 453 nm.

Example 6

Chemical Analysis of Labeled PLB

Labeled WT-PLB is analyzed according to Mueller et al., (2004) *Biochemistry* 43, 8754-8765. PLB derivatives are synthesized following the same procedure. Briefly, Mass spectra are acquired with a Bruker Biflex III matrix-assisted laser MALDI-TOF systems equipped with a nitrogen laser (337 nm, 3 ns pulse length) and a microchannel plate detector. Labeled PLB samples are co-crystallized from a stock solution in methanol with the matrix sinapinic acid. The data are collected in the linear mode, positive polarity, with an accelerating potential of 19 kV. Each spectrum is an accumulation of 100-400 laser shots. Amino acid analysis is carried out to confirm peptide composition and concentration. Purified DAB-WT-PLB is stored in methanol in the dark at <–60° C. until use for reconstitution.

Example 7

Reconstitution of Labeled SERCA and PLB

For intermolecular FRET, IAEDANS-SERCA was reconstituted with DABCYL-PLB essentially as described previously (see Reddy et al., (1999) *J. Biol. Chem.* 274:7649-7655; Reddy et al., (1995) *J. Biol. Chem.* 270:9390-9397; Reddy et al., (1996) *J. Biol. Chem.* 271:14964-14970) but adapted to modify the SERCA membrane concentration (molar ratio, SERCA/1000 lipids) and PLB-to-SERCA ratio (molar ratio PLB/SERCA). The desired amount of DABCYL-PLB in methanol and lipids (DOPC and DOPE, 4:1 weight ratio in chloroform) were gently mixed and dried over nitrogen gas to create a thin film. Residual solvent was removed under vacuum and desiccant overnight. Lipids and peptides were solubilized in reconstitution buffer (5 mM $MgCl_2$, 0.1M KCl, 10% glycerol, 20 mM MOPS, pH 7.0) by vortexing thoroughly, followed by mild sonication for 30 seconds to form unilamellar vesicles. $C_{12}E_8$ (2 mg/mg of lipid) was added to the tube. Detergent was removed over a 3 hour period using Biobeads SM2 (25 mg/mg of $C_{12}E_8$). FRET was measured immediately following reconstitution. Samples were frozen until gel electrophoresis.

Example 8

FRET Measurements and Data Analysis

The compound library was at an initial concentration of 10 mM in DMSO. Each compound was diluted to 10 μM in DMSO by serial dilutions to create daughter plates using 384-well plates. Each compound was analyzed in duplicate in the presence and absence of PLB. For each set of compounds, there was a pair of plates, one containing donor only, and the other containing donor plus acceptor. The compound was incubated for 20 minutes before the plate was read.

The plates were read at 25° C. using a Gemini EM fluorescence microplate reader, with bottom excitation at 350 nm (6 flashes). The spectra were obtained with 10 nm resolution between 420 and 600 nm (PMT sensitivity set to High). Total read time per plate was estimated to be 20 minutes.

The free calcium concentration, $[Ca^{2+}]$, was controlled by Ca/EGTA buffering, calculated by the method disclosed in Fabiato et al., (1979) *J. Physiol.* (*Paris*) 75:463-505. Measurements were conducted in low-Ca (pCa 6.5) buffer (50 mM KCl, 5 mM $MgCl_2$, 0.5 mM EGTA, 210 μM $CaCl_2$, 50 mM MOPS, pH 7.0), where the inhibitory effect of PLB was maximal.

The fluorescence resonance energy transfer efficiency (E) was calculated from the fractional decrease of steady-state emission of the donor ($F_D$) due to the presence of the acceptor ($F_{DA}$):

$$E = 1 - \frac{F_{DA}}{F_D}$$

The donor-acceptor distance R in the saturated SERCA-PLB complex is calculated from $$R=R_0(E^{-1}-1)^{1/6}$$

Where the Förster distance $R_0$ of this dye pair was calculated to be 32 Å from $$R_0=9780(Jk^2n^{-4}\phi_D)^{1/2}$$

where n is the refractive index of protein in aqueous solution (1.33), k is the orientation factor (set to ⅔, corresponding to random orientation), and $\phi_D$ is the donor quantum yield (0.36 for AEDANS). J is the normalized spectral overlap integral of donor emission $F_D(\lambda)$ and acceptor excitation $\epsilon$-($\lambda$)

$$J = \frac{\int F_D(\lambda)\varepsilon(\lambda)\lambda^4 d\lambda}{\int F_D(\lambda) d\lambda}$$

and was calculated by numerical integration using a Microcal Origin 7.0 template.

Example 9

Steady-State FRET Measurement and Data Analysis

Steady-state FRET experiments used Alexa Fluor 488-FKBP and Alexa Fluor 568-CaM as a donor-acceptor pair (R0=62 Å). SR membranes (0.4 mg/mL) were preincubated with the F-FKBP (50 nM) for 90 min in the KCl/Pipes-binding buffer. Membranes were centrifuged at 100,000×g to remove unbound F-FKBP donor, and the pellet was resuspended to a final concentration of 3 mg/mL. FRET was measured following 2.5-h incubations at 25° C. in the same buffer containing 0-800 nM F-CaM acceptor. Steady-state fluorescence emission spectra were acquired in 384-well, optical-bottom, black plates by using a Gemini EM microplate fluorometer (Molecular Devices) with excitation at 490 nm and a 495-nm emission long-pass filter.

Example 10

Time-Resolved FRET Measurement and Data Analysis

Time-resolved FRET was performed following a procedure modified from Cornea et al., (2009) *Proc. Natl. Acad. Sci. USA* 06(15):6128-6133. Briefly, IAEDANS and TNP-ADP were used in the time-resolved FRET experiments. Fluorescence was excited with a nanosecond laser pulse and detected with subnanosecond resolution using a custom fluorometer built by Igor Negrashov in collaboration with Fluorescence Innovations Inc. Excitation at 355 nm was provided by a 9-kHz, frequency-tripled, Q-switched microchip YAG laser (NanoUV-355; JDS Uniphase), and emission was directly converted to digital form via an 8-bit, 0.125 ns per channel DS252 digitizer (Acqiris, Geneva, Switzerland). Full fluorescence waveforms were acquired after each laser pulse with 0.2 ns per data point resolution. The instrument-response function was acquired by detecting light scattering with the same instrument settings as for the samples. Lifetimes were determined from time-resolved fluorescence, which was analyzed by using a multiexponentila function:

$$F(t) = F_0 \sum_{i=1}^{n} x_i e^{-t/\tau i}$$

where $\tau_i$ and $x_i$ are the excited-state lifetimes and mole fractions, respectively. This function was convoluted with the instrument-response function and fit to the experimental data. $F_0$, $\tau_i$ and $x_i$ were varied to minimize $\chi^2$, increasing n until there was no significant decrease in $\chi^2$ with further increase in n. This typically resulted for n=3. Distance measurements assumed random orientation of fluorophores. This assumption is supported by the agreement of distance measurements with different donor-acceptor pairs.

Example 11

ATPase Measurements and Data Analysis

ATPase activity was measured using an NADH-linked, enzyme-coupled microtiter plate assay (200 μL/well) as described in Karim et al., (2000) *J. Biol. Chem.* 276, 38814-9 and Reddy et al., (2003) Biochemistry 42, 4585-92. [Ca2+] was controlled by Ca/EGTA buffering by the method described in Fabiato et al., (1979) *J. Physiol.* (*Paris*) 75:463-

505. The assays were detected at 340 nm on a Spectramax Plus microplate spectrophotometer (Molecular Devices) at 25° C. in the presence of ionophore A23187 to dissipate the Ca gradient building up across the membranes due to ATPase activity. The data were plotted (V vs pCa) and fitted by the Hill equation:

$$V = \frac{V_{max}}{1 + 10^{-n(pK_{Ca} - pCa)}}$$

where V is the initial ATPase rate and n is the Hill coefficient. Data were normalized to the maximal rate, Vmax, which was obtained from the fit, and replotted to determine the shift in $pK_{Ca}$.

Table 1 shows the effect of a compound CDN1001 isolated using HTS as in Examples 1, 3, 4, 5, 6, 7 and 8 above, on ATPase activity of SERCA1a and SERCA2a in the presence PLB. Compared to the control where no compound was present, CDN1001 increased the $V_{max}$ values for both SERCA1a and SERCA2a.

TABLE 1

Effect of 10 μM CDN1001 on SERCA ATPase activities (% increase in $V_{max}$).

| | |
|---|---|
| Cardiac SR (SERCA2a + PLB) | 8.1% ± 1.1% (n = 14, p = 0.00001) |
| Skeletal SR (SERCA1a) | 21.2% ± 5.7% (n = 13, p = 0.001) |

Example 12

Functional Potency and FRET Potency of WT-PLB and PLB Derivatives

Functional potency was measured by ATPase assay as $\Delta pK_{Ca}$, which stands for the shift in pCa value required for 50% activation of SERCA, at a ratio of 5 PLB/SERCA. FRET potency was measured as E(5), the energy transfer efficiency found at a ratio of 5 PLB/SERCA (N=4-6, mean±SEM). WT-PLB was found to be more suitable for HTS, based on its moderate functional potency and FRET potency comparable to that of I40A, the PLB derivative used in the published method of Mueller et al. (2004) *Biochemistry* 43:8754-8765.

TABLE 2

Functional and FRET potency of WT-PLB and PLB derivatives.

| | PLB variant | | | |
|---|---|---|---|---|
| | L31A | S16E | WT | I40A |
| Functional potency ($\Delta pK_{Ca}$) | 0.05 ± 0.01 | 0.07 ± 0.02 | 0.18 ± 0.02 | 0.48 ± 0.03 |
| FRET potency | 0.45 ± 0.03 | 0.69 ± 0.02 | 0.60 ± 0.03 | 0.69 ± 0.03 |

Example 13

Competition of WT-PLB and PLB Derivatives to Optimize Functional Potency and FRET Potency The competition of WT-PLB and PLB derivatives was assessed by ATPase activity (e.g., Example 11) and FRET assays (e.g., Example 8). A reconstituted sample containing 5 moles of acceptor-labeled active PLB (WT or I40A) and 5 moles of an unlabeled loss-of-function (LOF) mutant (L31A or S16E) per mole of SERCA was compared with a control, a reconstituted sample with 5 moles of an active PLB (WT or I40A) per mole of SERCA. Competition was measured as the fractional decrease in ΔpKCa or FRET efficiency E, due to the presence of the LOF mutant (N=3-6, mean±SEM). The interaction of WT-PLB with SERCA was found to be more easily disrupted (therefore useful for HTS) by loss-of-function (LOF) mutants, compared with I40A-PLB, which was used in the published method of Mueller et al. (2004) *Biochemistry* 43:8754-8765.

TABLE 3

Competition of LOF mutants in the presence of WT or I40A-PLB.

| | PLB variant | | | |
|---|---|---|---|---|
| | WT | WT | I40A | I40A |
| | PLB competitor | | | |
| | L31A | S16E | L31A | S16E |
| Functional relief | 0.79 ± 0.04 | 0.83 ± 0.05 | 0.47 ± 0.06 | 0.40 ± 0.03 |
| FRET relief | 0.37 ± 0.06 | 0.27 ± 0.10 | 0.18 ± 0.12 | 0.15 ± 0.08 |

Such a competitive assay can be used to optimize functional potency. Use of this PLB competition assay is an example of a method that provides a means to identify the components required to transform a FRET assay into one that is amenable to a HTS assay, for identifying molecules that modulate the SERCA-PLB complex or its microenvironment in a membrane.

Example 14

Comparison of FRET Sensitivity Using WT-PLB and I40A-PLB and Amino Acid Site of PLB Label FRET assays using WT-PLB labeled at Lysine-0 or I40A-PLB labeled at Lysine-3 are performed according to the procedure in Example 1.

A compound, CDN1001, isolated using HTS as in Examples 1, 3, 4, 5, 6, 7 and 8 above. Table 4 show that the decrease in FRET by CDN1001 is negligible when measured by the published method of Mueller et al. (2004) *Biochemistry* 43:8754-8765, which used I40A-PLB labeled at Lysine-3, but is significant when measured using the current procedure, in which both functional potency and FRET potency have been optimized, and which uses WT-PLB labeled at Lysine-0. Therefore, SERCA2 binding by compounds can be detected with a FRET assay, that is optimized for HTS as described herein, that modulate the SERCA-PLB complex or its microenvironment in a membrane, but not by the published method of Mueller et al. (2004).

TABLE 4

A comparison of decrease in FRET using WT-PLB and I40A-PLB by 10 uM CDN1001

| Acceptor | % decrease in FRET |
|---|---|
| Dabcyl-K3-I40A-PLB | 2.3% ± 1.8% (n = 3, p = 0.4) |
| Dabcyl-K0-WT-PLB | 7.9% ± 2.2% (n = 5, p = 0.01) |

The contents of all references described herein are hereby incorporated by reference.

Other embodiments are within the following claims.

What is claimed is:

1. A method for identifying a compound that modulates Sarco/Endoplasmic Reticulum Calcium ATPase (SERCA), comprising:

(a) providing, in the presence of one or more lipids, SERCA labeled with a first chromophore at a first position and a second chromophore at a second position, wherein the second position is different from the first position, wherein the first and the second chromophores can be used for Fluorescence Resonance Energy Transfer (FRET), and wherein the method is suitable for high-throughput screening (HTS);

(b) exciting either the first or the second chromophore; and (c) measuring FRET between the chromophores;

wherein a difference between FRET in the presence of a test compound and FRET in the absence of the test compound indicates that the test compound modulates SERCA, such that the energy transfer between the two chromophores is altered.

2. The method of claim 1, wherein the method is performed in the presence of phospholamban (PLB).

3. A method for identifying a compound that modulates the SERCA-PLB complex or its microenvironment, comprising:

(a) providing SERCA labeled with a first chromophore;

(b) providing PLB labeled with a second chromophore, wherein the PLB is WT-PLB or a PLB derivative that gives a functional potency and FRET potency suitable for HTS, and wherein the chromophores can be used for energy transfer;

(c) contacting the SERCA of step (a) with the PLB of step (b) in the presence of a test compound and one or more lipids;

(d) exciting either the first or the second chromophore; and (e) measuring FRET between the chromophores;

wherein a difference between FRET in the presence of the test compound and FRET in the absence of the test compound indicates that the test compound modulates the SERCA-PLB complex or its microenvironment, such that the energy transfer between the two chromophores is altered.

4. The method of claim 2, wherein the molar ratio of SERCA to PLB ranges from about 1 to 10 to about 10 to 1.

5. The method of claim 3, wherein the molar ratio of SERCA to PLB ranges from about 1 to 10 to about 10 to 1.

6. The method of claim 1, wherein the SERCA is at a concentration ranging from about 1 nM to about 200 μM.

7. The method of claim 2, wherein the SERCA is at a concentration ranging from about 1 nM to about 200 μM.

8. The method of claim 3, wherein the SERCA is at a concentration ranging from about 1 nM to about 200 μM.

9. The method of claim 2, wherein the PLB is at a concentration ranging from about 1 nM to about 200 μM.

10. The method of claim 3, wherein the PLB is at a concentration ranging from about 1 nM to about 200 μM.

11. The method of claim 3, wherein the PLB derivative comprises one or more of amino acid modifications relative to WT-PLB, and wherein the amino acid substitutions are one or more of substitution of serine to glutamate at position 16, substitution of leucine to alanine at position 31, substitution of cysteine to alanine at position 36, substitution of isoleucine to alanine at position 40 and substitution of cysteine to phenylalanine at position 41.

12. The method of claim 1, wherein the first chromophore is labeled on a cysteine residue, and wherein the second chromophore is labeled on a lysine residue.

13. The method of claim 2, wherein the first chromophore is labeled on a cysteine residue, and wherein the second chromophore is labeled on a lysine residue.

14. The method of claim 3, wherein the first chromophore is labeled on a cysteine residue, and wherein the second chromophore is labeled on a lysine residue.

15. The method of claim 1, wherein the first chromophore is N,N,N',N'-tetramethyl-6-carboxyrhodamine, 5-((((2-iodoacetyl)amino)ethyl)amino) naphthalene-1-sulfonic acid (IAEDANS) and the second chromophore is 4-((4-(dimethylamino)phenyl)azo)benzoic acid (DABCYL) or 2'-(or-3')-0-(trinitrophenyeadenosine 5'-diphosphate (TNP-ADP).

16. The method of claim 2, wherein the first chromophore is IAEDANS and the second chromophore is DABCYL or TNP-ADP.

17. The method of claim 3, wherein the first chromophore is IAEDANS and the second chromophore is DABCYL or TNP-ADP.

18. The method of claim 2, wherein the method is performed in the presence of one or more lipids, wherein the molar ratio of lipids to PLB to SERCA is about 100-6000 to 1-10 to 1-10.

19. The method of claim 3, wherein the molar ratio of lipids to PLB to SERCA is about 100-6000 to 1-10 to 1-10.

20. A kit for identifying a test compound that modulates the SERCA-PLB complex or its microenvironment, comprising:

(a) SERCA labeled with a first chromophore; and (b) PLB labeled with a second chromophore;

wherein the PLB is WT-PLB or a PLB derivative that gives a FRET potency suitable for HTS, and wherein the chromophores can be used for energy transfer.

* * * * *